(12) United States Patent
Langlois et al.

(10) Patent No.: US 9,052,255 B2
(45) Date of Patent: Jun. 9, 2015

(54) SYSTEM FOR AUTONOMOUS MONITORING OF BIOAGENTS

(75) Inventors: Richard G. Langlois, Livermore, CA (US); Fred P. Milanovich, Lafayette, CA (US); Billy W. Colston, Jr., San Ramon, CA (US); Steve B. Brown, Livermore, CA (US); Don A. Masquelier, Tracy, CA (US); Raymond P. Mariella, Jr., Danville, CA (US); Kodomudi Venkateswaran, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 853 days.

(21) Appl. No.: 12/786,248

(22) Filed: May 24, 2010

(65) Prior Publication Data

US 2011/0027781 A1 Feb. 3, 2011

Related U.S. Application Data

(62) Division of application No. 10/643,797, filed on Aug. 19, 2003, now abandoned.

(60) Provisional application No. 60/406,159, filed on Aug. 26, 2002.

(51) Int. Cl.

| | |
|---|---|
| *G01N 33/543* | (2006.01) |
| *G01N 30/96* | (2006.01) |
| *G01N 33/00* | (2006.01) |
| *G01N 1/22* | (2006.01) |
| *G01N 35/08* | (2006.01) |
| *G01N 15/14* | (2006.01) |

(52) U.S. Cl.
CPC ............ *G01N 1/2202* (2013.01); *G01N 1/2211* (2013.01); *G01N 35/08* (2013.01); *G01N 2001/2217* (2013.01); *G01N 15/1459* (2013.01)

(58) Field of Classification Search
None
See application file for complete search history.

(56) References Cited

U.S. PATENT DOCUMENTS

| | | | |
|---|---|---|---|
| 6,100,084 A | 8/2000 | Miles et al. | |
| 6,122,396 A | 9/2000 | King et al. | |
| 6,235,471 B1 | 5/2001 | Knapp et al. | |
| 6,363,803 B1 | 4/2002 | Hubers | |
| 6,368,871 B1 | 4/2002 | Christel et al. | |

(Continued)

FOREIGN PATENT DOCUMENTS

| | | |
|---|---|---|
| WO | WO 98/26295 | 6/1998 |
| WO | WO 00/73413 | 12/2000 |

(Continued)

OTHER PUBLICATIONS

Langlois et al. ("Autonomous Pathogen Detection System" RI-LLNL, UCRL-ID-142227, Jan. 2001).*

(Continued)

*Primary Examiner* — Chris L Chin
(74) *Attorney, Agent, or Firm* — Eddie E. Scott

(57) ABSTRACT

An autonomous monitoring system for monitoring for bioagents. A collector gathers the air, water, soil, or substance being monitored. A sample preparation means for preparing a sample is operatively connected to the collector. A detector for detecting the bioagents in the sample is operatively connected to the sample preparation means. One embodiment of the present invention includes confirmation means for confirming the bioagents in the sample.

2 Claims, 14 Drawing Sheets

(56) References Cited

U.S. PATENT DOCUMENTS

| | | | |
|---|---|---|---|
| 6,369,893 | B1 | 4/2002 | Christel et al. |
| 6,374,684 | B1 | 4/2002 | Dority |
| 6,391,541 | B1 | 5/2002 | Petersen et al. |
| 6,403,037 | B1 | 6/2002 | Chang et al. |
| 6,406,893 | B1 | 6/2002 | Knapp et al. |
| 6,431,476 | B1 | 8/2002 | Taylor et al. |
| 6,440,725 | B1 | 8/2002 | Pourahmadi et al. |
| 6,524,532 | B1 | 2/2003 | Northrup |
| 6,576,459 | B2 * | 6/2003 | Miles et al. ............ 435/286.5 |
| 6,787,104 | B1 * | 9/2004 | Mariella, Jr. ............ 422/4 |
| 6,887,710 | B2 * | 5/2005 | Call et al. ............ 436/53 |
| 2002/0123048 | A1 | 9/2002 | Gau |
| 2002/0187470 | A1 * | 12/2002 | Casey et al. ............ 435/6 |
| 2003/0032172 | A1 | 2/2003 | Colston, Jr. et al. |
| 2006/0057599 | A1 | 3/2006 | Dzenitis et al. |

FOREIGN PATENT DOCUMENTS

| | | |
|---|---|---|
| WO | WO 01/06248 | 1/2001 |
| WO | WO 03/027325 | 4/2003 |

OTHER PUBLICATIONS

Belgrader et al. ("Autonomous system for pathogen detection and identification" RI-LLNL, UCRL-JC-128919, 1998, pp. 1-11, also in SPIE Proceedings, 3533, 1998, pp. 198-206).*

Marple, V. A., Olson, B. A., & Rubow, K. L. (2001). Inertial, gravitational, centrifugal, and thermal collection techniques. In P. A. Baron, & K. Willeke (Eds.), Aerosol measurement, principles, techniques, and applications (2nd ed.). New York: Wiley-lnterscience (pp. 229-260).*

Langlois et al. ("Development of an autonomous pathogen detection system" Proceedings of the first joint conference on point detection, Wlliamsburg, VA, Oct. 2000).*

Vignali ("Multiplexed particle-based flow cytometric assays", Journal of Immunological Methods 243 (2000) 243-255).*

Cole, S., "Biodetectors Evolving, Monitoring U.S. Cities," Homeland Security Solutions, http:hss.pennnet.com/Articles/Article_Display.cfm?Section=Articles&Subsection=Displa..., May 2003, 3 pages, PennWell Corporation.

Dutton, G., "Detecting Biowarfare Weapons Developing Systems to Combat Bioterrorism," Gilder Biotech Report, http://www.gilderbiotech.com/Articles/Bioterror/DetectingBiowarfare.htm, 2002, 6 pages, Gilder Publishing, Great Barrington, MA 01230.

Pettit, S., "EWU Researcher Developing Bioterrorism Defense Equipment; Testing to Detect Simulated Airborne Pathogens Scheduled for January," Eastern Washington University, http://www.ewu.edu/NewsEventsAlumni/NewsServ/research-10-22-01.html, Oct. 22, 2001, 3 pages.

Young, D., "First Alert," Government Computer News, http://www.gcn.com/state/vol7_no5/tech-report/1027-1.html, May 2001, vol. 7, No. 5, 3 pages.

No Author, "MicroFluidic Systems Inc. Secures Increased Funding to Develop Autonomous Pathogen Detection Systems," Infection Control Today, http://www.infectioncontroltoday.com/hotnews/33h208659.html, Mar. 20, 2003, 3 pages, Virgo Publishing, Inc.

Miller, J., "U.S. Is Deploying a Monitor System for Germ Attacks," The New York Times, http://www.nytimes.com/2003/01/22/national/22DISE.html?ei=1&en=..., Jan. 22, 2003, 3 pages.

* cited by examiner

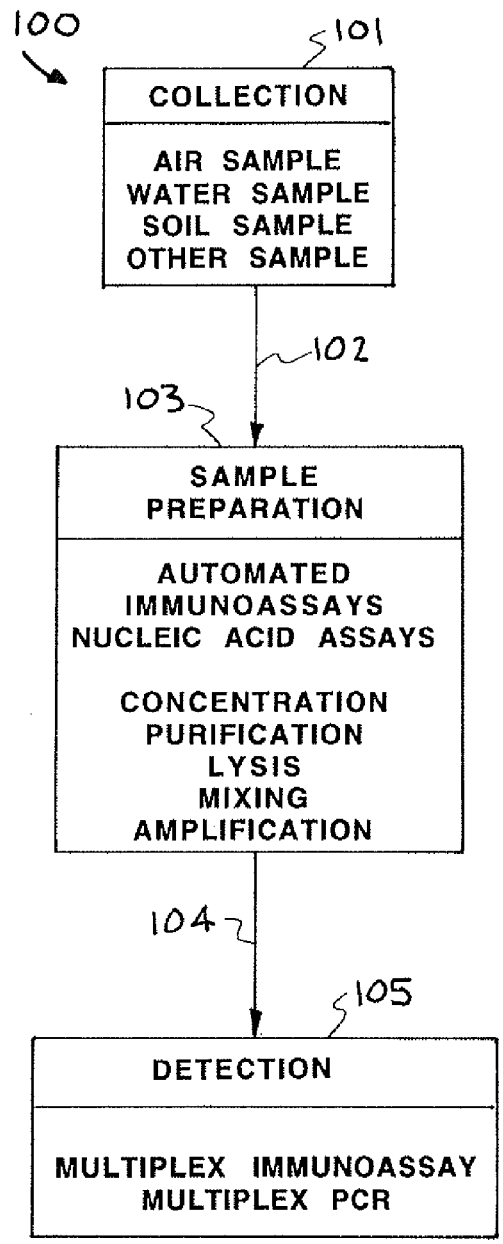
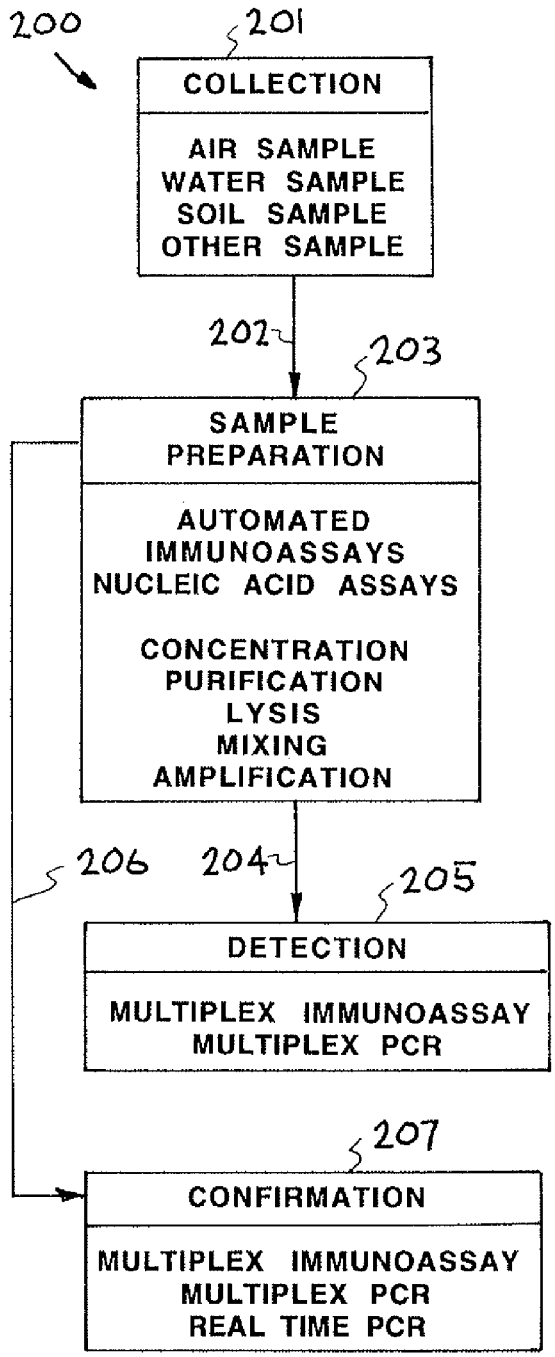
FIG. 1
FIG. 2

```
                    ┌──────────────┐
              301 ──│   AEROSOL    │────────300
                    │  COLLECTION  │
                    └──────┬───────┘
                           │
                           ▼
                    ┌──────────────┐
              302 ──│   IN-LINE    │
                    │    SAMPLE    │
                    │ PREPARATION  │
                    └──────┬───────┘
                           │
              303          ▼
            ┌───────────────────────────┐
            │  DETECTION-LIQUID-ARRAY   │
            │   BASED MULTIPLEX         │
            │  IMMUNOASSAY DETECTION    │
            │  AND/OR NUCLEIC ACID      │
            │   ASSAYS DETECTION        │
            └───────────┬───────────────┘
                        │
              304       ▼
            ┌───────────────────────────┐
            │  CONFIRMATION-IN-LINE     │
            │    NUCLEIC ACID           │
            │  AMPLIFICATION AND        │
            │     DETECTION             │
            └───────────────────────────┘

305
                            ┌───────────────────┐
                            │    INTEGRATED     │
                            │  REMOTE CONTROL   │
                            │   AND FEEDBACK    │
                            └───────────────────┘
```

FIG. 3

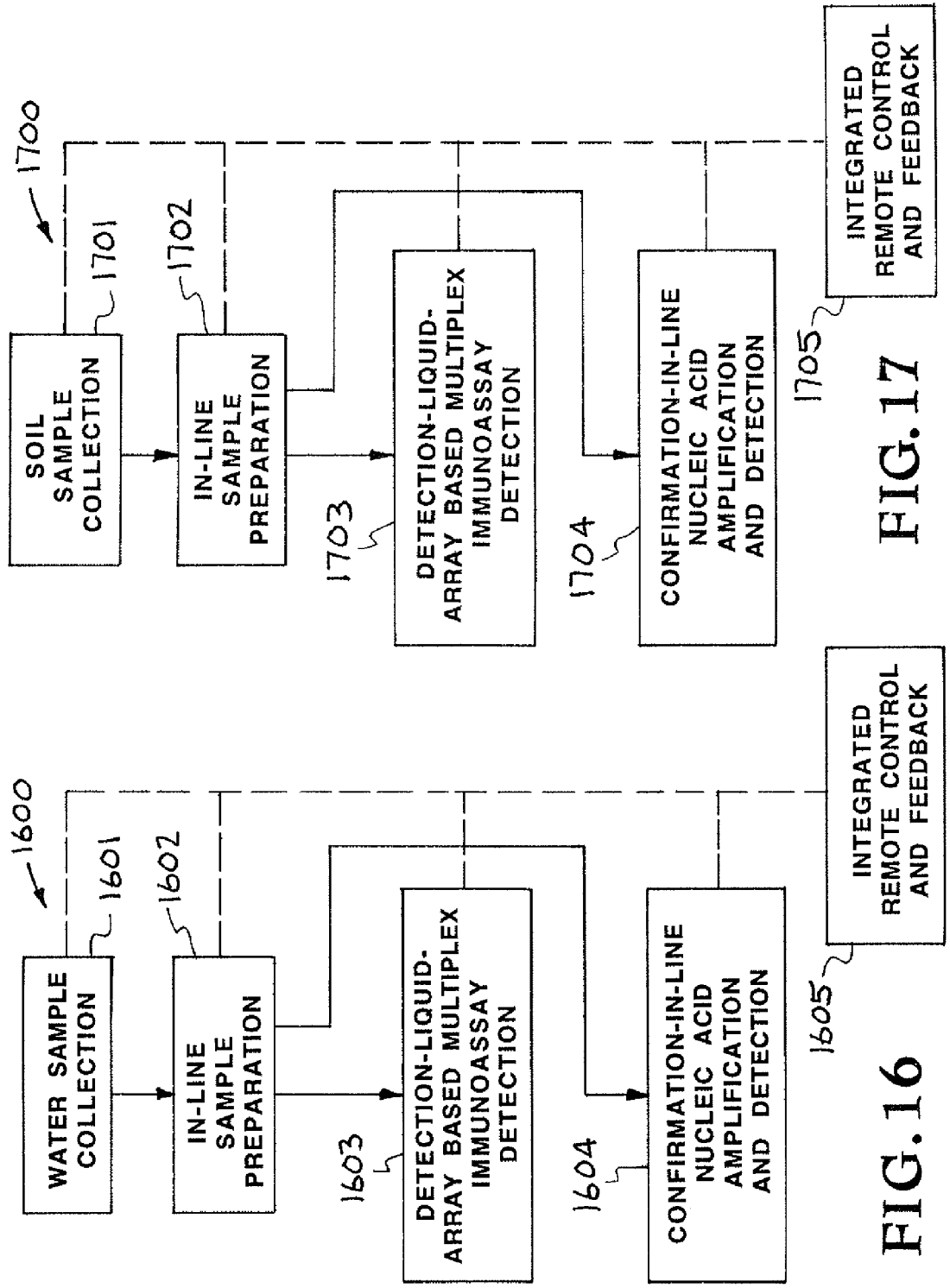

SYSTEM FOR AUTONOMOUS MONITORING OF BIOAGENTS

CROSS-REFERENCE TO RELATED APPLICATIONS

This application is a Divisional of application Ser. No. 10/643,797 filed Aug. 19, 2003 now abandoned, entitled "System for Autonomous Monitoring of Bioagents". This application claims the benefit of U.S. Provisional Patent Application No. 60/406,159, filed Aug. 26, 2002, and titled "System for Autonomous Monitoring of Bioagents", which are incorporated herein by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to bioagents and more particularly to monitoring bioagents.

2. State of Technology

There exists a critical need to develop distributed biothreat agent sensor networks that can operate in civilian applications. To operate in "Detect to Protect/Warn" type detection architectures, these platforms need to have several key properties. They need to be capable of detecting pathogens within a 1-2 hour time window, allowing for enough time to respond to an event. They need to be extremely low cost to maintain, since continuous monitoring is essential for many applications. These platforms need to have sufficient sensitivity to cover a broad geographical area (limiting the necessary number of sensors) and have sufficient selectivity to virtually eliminate false positives. Currently available bio-weapons detection systems are designed primarily for military use on the battlefield. These systems are often expensive to deploy and ultimately unsuited for civilian protection.

In an article titled, "U.S. Is Deploying a Monitor System for Germ Attacks," by Judith Miller in *The New York Times* on Jan. 22, 2003, it was reported, "To help protect against the threat of bioterrorism, the Bush administration on Wednesday will start deploying a national system of environmental monitors that is intended to tell within 24 hours whether anthrax, smallpox and other deadly germs have been released into the air, senior administration officials said today. The system uses advanced data analysis that officials said had been quietly adapted since the September 11 attacks and tested over the past nine months. It will adapt many of the Environmental Protection Agency's 3,000 air quality monitoring stations throughout the country to register unusual quantities of a wide range of pathogens that cause diseases that incapacitate and kill . . . . The new environmental surveillance system uses monitoring technology and methods developed in part by the Department of Energy's national laboratories. Samples of DNA are analyzed using polymerase chain reaction techniques, which examine the genetic signatures of the organisms in a sample, and make rapid and accurate evaluations of that organism . . . . Officials who helped develop the system said that tests performed at Dugway Proving Ground in Utah and national laboratories showed that the system would almost certainly detect the deliberate release of several of the most dangerous pathogens. 'Obviously, the larger the release, the greater the probability that the agent will be detected,' an official said. But given the coverage provided by the E.P.A. system, even a small release, depending on which way the wind was blowing and other meteorological conditions, is likely to be picked up.'"

In an article titled, "Biodetectors Evolving, Monitoring U.S. Cities," by Sally Cole in the May 2003 issue of *Homeland Security Solutions*, it was reported, "The anthrax letter attacks of 2001, and subsequent deaths of five people, brought home the reality of bioterrorism to Americans and provided a wake-up call for the U.S. government about the need for a method to detect and mitigate the impact of any such future attacks. Long before the anthrax letter attacks, scientists at two of the U.S. Department of Energy's national laboratories, Lawrence Livermore National Laboratory (LLNL) and Los Alamos National Laboratory (LANL), were busy pioneering a "biodetector" akin to a smoke detector to rapidly detect the criminal use of biological agents. This technology is now expected to play a large role in the U.S. government's recently unveiled homeland security counter-terrorism initiative, Bio-Watch, which is designed to detect airborne bioterrorist attacks on major U.S. cities within hours. Announced back in January, Bio-Watch is a multi-faceted, multi-agency program that involves the U.S. Department of Energy, the Environmental Protection Agency (EPA), and the U.S. Department of Health and Human Services' Centers for Disease Control and Prevention (CDC). Many of the EPA's 3,000 air-quality monitoring stations throughout the country are being adapted with biodetectors to register unusual quantities of a wide range of pathogens that cause diseases that incapacitate and kill, according to the EPA. The nationwide network of environmental monitors and biodetectors, which reportedly will eventually monitor more than 120 U.S. cities, is expected to detect and report a biological attack within 24 hours. Citing security reasons, the EPA declined to disclose further details about the program at this time. . . . The Autonomous Pathogen Detection System (APDS) is file-cabinet-sized machine that sucks in air, runs tests, and reports the results itself. APDS integrates a flow cytometer and real-time PCR detector with sample collection, sample preparation, and fluidics to provide a compact, autonomously operating instrument capable of simultaneously detecting multiple pathogens and/or toxins. The system is designed for fixed locations, says Langlois, where it continuously monitors air samples and automatically reports the presence of specific biological agents. APDS is targeted for domestic applications in which the public is at high risk of exposure to covert releases of bioagents—subway systems, transportation terminals, large office complexes, and convention centers . . . . APDS provides the ability to measure up to 100 different agents and controls in a single sample,' Langlois says. 'It's being used in public buildings right now.' The latest evolution of the biodetector, APDS-II, uses bead-capture immunoassays and a compact flow cytometer for the simultaneous identification of multiple biological stimulants. Laboratory tests have demonstrated the fully autonomous operation of APDS-II for as long as 24 hours, . . . ."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for monitoring air for bioagents. Particles in the air are separated by size and the particles of a size range that are likely to contain the bioagents are collected. Any bioagents in the collected particles are detected by a detector system. One embodiment of the present invention includes confirming the bioagents by adding a PCR reagent to the particles, performing PCR amplification on the particles, and detecting PCR amplicon.

One embodiment of the present invention provides an autonomous bioagent monitoring apparatus for monitoring air, water, soil, or other substance for bioagents. A collector gathers the air, water, soil, or other substance being monitored. A sample preparation means for preparing a sample is operatively connected to the collector. A detector for detecting the bioagents in the sample is operatively connected to the sample preparation means. One embodiment of the present invention includes confirmation means for confirming the bioagents in the sample.

In one embodiment, the present invention provides an autonomous monitoring apparatus for monitoring air, water, soil, or other substance for bioagents. A collector gatherings the air, water, soil, or other substance being monitored. The collector separates selected potential bioagent particles from the air, water, soil, or other substance. Sample preparation means prepares a sample of the selected potential bioagent particles. The sample preparation means is operatively connected to the collector for preparing the sample from the air, water, soil, or other substance gathered by the collector. A detector detects the bioagents in the sample. The detector is operatively connected to the sample preparation means.

In one embodiment the collector includes a wetted-wall cyclone collector that receives product air flow and traps and concentrates potential bioagent particles of a predetermined particle size range in a liquid. In one embodiment the sample preparation means includes means for injecting and/or aspirating a sample, means for adding a reagent to the sample, means for mixing the sample and the reagent, and means for transporting the sample and the reagent. In one embodiment microbeads are optically encoded and the optically encoded microbeads are interrogated by a laser in detecting bioagents in the sample.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 1 is a block diagram illustrating an embodiment of an autonomous pathogen detection system constructed in accordance with the present invention.

FIG. 2 is a block diagram illustrating another embodiment of an autonomous pathogen detection system constructed in accordance with the present invention.

FIG. 3 is a block diagram illustrating a specific embodiment of the invention designated as an AUTONOMOUS PATHOGEN DETECTION SYSTEM (APDS).

FIG. 16 is a block diagram illustrating another embodiment of an autonomous pathogen detection system constructed in accordance with the present invention.

FIG. 17 is a block diagram illustrating another embodiment of an autonomous pathogen detection system constructed in accordance with the present invention.

DETAILED DESCRIPTION OF THE INVENTION

Figure 4:
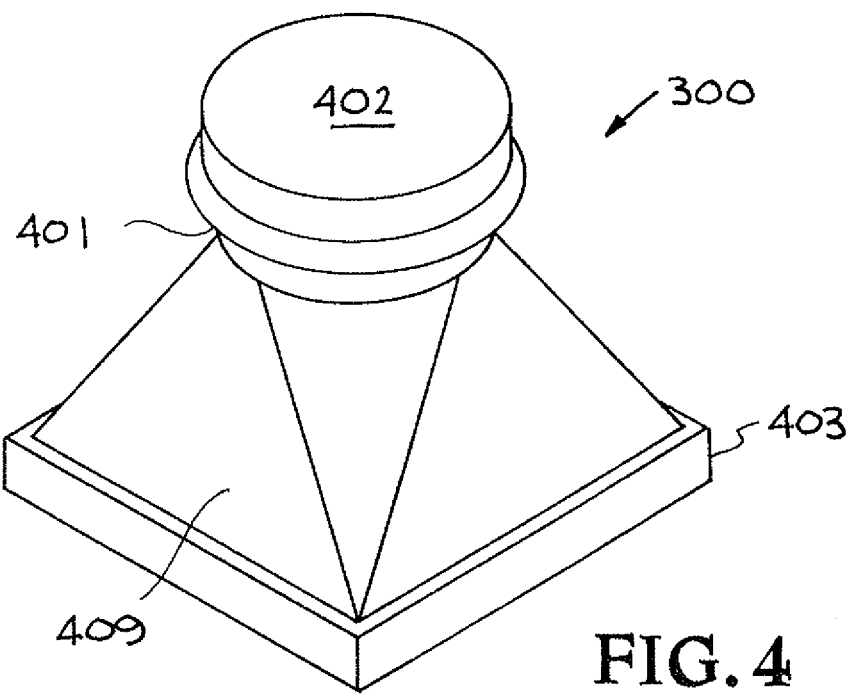
FIG. 4 is an illustration that shows the aerosol collection system.

Referring now to the drawings, to the following detailed description, and to incorporated materials, detailed information about the present invention is provided including the description of specific embodiments. The detailed description and the specific embodiments serve to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Terrorists sending anthrax-contaminated packages. Militant organizations obtaining potassium cyanide. Religious cult members poisoning local residents to fix an election. Sadly, these scenarios are not the plots of the three latest bestsellers, but rather, very real incidents with a very real danger. By the mid-1990s, the U.S. Congress began to assess the vulnerability of the U.S. civilian population to biological terrorism and found us considerably lacking in our ability to cope with even a small-scale biological event. Initial thinking was that Department of Defense technology could be readily transferred to the civilian arena. However, upon further reflection, it was concluded that although there was overlap between military and civilian defense needs, in the case of a biological threat, there are marked differences: (1) the soldier is trained and equipped with protective gear so he may respond to a threat quickly enough to prevent a lethal dose; (2) military intelligence usually reduces the potential threat to a relatively small number of biological agents; and, (3) military battlefield tactics are designed to minimize the density of soldiers. The civilian population, however, is neither trained nor equipped, is vulnerable to any conceivable pathogen and often gathers in large crowds (special events, sporting venues, etc.) where a small release could potentially infect thousands. In response to these differences, federal agencies, including Department of Energy, have recently begun funding directed research efforts to reduce civilian biological terrorist vulnerabilities.

At present there are more than 30 pathogens and toxins on various agency threat lists. Public health personnel rarely see most, of the pathogens so they have difficulty identifying them quickly. In addition, many pathogenic infections aren't immediately symptomatic, with delays as long as several days, limiting options to control the disease and treat the patients. The lack of a practical monitoring network capable of rapidly detecting and identifying multiple pathogens or toxins on current threat lists translates into a major deficiency in the United States ability to counter biological terrorism.

Referring now to FIG. 1, an embodiment of an autonomous pathogen detection system constructed in accordance with the present invention is illustrated by a block diagram. The autonomous pathogen detection system is designated generally by the reference numeral 100. The autonomous pathogen detection system 100 provides collection 100, sample preparation 103, and detection 105. The collection 101 includes gathering air, water, soil or other substance to provide an air sample, water sample, soil sample or a sample of other substances.

After the collection 100, the sample is transferred as shown by arrow 102 for sample preparation 103. The sample preparation 103 provides an automated sample, an immunoassays sample, and/or a nucleic acid assays sample. In sample preparation 103 the sample may be concentrated, purified, lisis of spores, mixed, and/or amplified.

After sample preparation 103, the sample is transferred as shown by arrow 104 for detection. In one embodiment of the autonomous pathogen detection system 100, the detection is by a multiplex immunoassay detector. In another embodiment of the autonomous pathogen detection system 100, the detection is by a multiplex PCR detector.

The autonomous pathogen detection system 100 provides an apparatus and method for monitoring air, water, soil, or other substance for particles containing bioagents. The autonomous pathogen detection system 100 comprises a collector for gathering the air, water, soil, or other substance being monitored; sample preparation means for preparing a sample from the air, water, soil, or other substance gathered by the collector; and a detector for detecting any bioagents in the sample. In one embodiment the collector is an aerosol collector. In other embodiments the collector gathers water, soil, or other substances. The collector in one embodiment includes separator means for separating the particles of interest from other particles. The particles of interest are of a predetermined size range.

In one embodiment the collector is an aerosol collector that collects air and includes means for separating the air into a bypass air flow that does not contain the particles of a predetermined particle size range and a product air flow that does contain the sample particles of a predetermined particle size range. A wetted-wall cyclone collector receives the product air flow and traps and concentrates the particles of a predetermined particle size range in a liquid.

In one embodiment the sample preparation means is automated. In one embodiment the sample preparation means provides an immunoassays sample. In anther embodiment the sample preparation means provides a nucleic acid assays sample. In another embodiment the sample preparation means provides the sample preparation means includes concentration of the air, water, soil, or other substance. In anther embodiment the sample preparation means provides the sample preparation means includes purification of the air, water, soil, or other substance. In anther embodiment the sample preparation means provides the sample preparation means includes lysis of the air, water, soil, or other substance. In anther embodiment the sample preparation means provides includes mixing of the air, water, soil, or other substance. In anther embodiment the sample preparation means provides includes amplification.

In one embodiment of the autonomous pathogen detection system 100, the detector is a multiplex immunoassay detector. In one embodiment of the autonomous pathogen detection system 100, the detector is a multiplex PCR detector.

The primary focus of the autonomous pathogen detection system 100 is the protection of civilians from terrorist attacks, however, the system also has a role in protecting military personnel from biological warfare attacks. The autonomous pathogen detection system 100 also has uses in medical facilities and research and development facilities. The autonomous pathogen detection system 100 has uses in medical monitoring. There are a variety of medical applications where monitoring for biological pathogens would be useful. A good example of this is monitoring in hospitals and clinics for highly infectious agents such as tuberculosis or nosocomial diseases that can threaten the well being of patients and health care professionals. The autonomous pathogen detection system 100 also has uses in environmental monitoring, that is, any application that would benefit from environmental monitoring of biological species. One example is continuous aerosol monitoring of bacterial and other pathogens that could affect the health of livestock (such as the recent hoof and mouth disease outbreak). Another example is continuous aerosol monitoring of viruses that could affect the health of large portions of the population (such as the recent SARS outbreak).

Referring now to FIG. 2, another embodiment of an autonomous pathogen detection system constructed in accordance with the present invention is illustrated by a block diagram. This embodiment of the autonomous pathogen detection system is designated generally by the reference numeral 200. The autonomous pathogen detection system 200 provides collection 200, sample preparation 203, detection 205, and confirmation 207. The collection 201 includes gathering air, water, soil or other substance to provide an air sample, water sample, soil sample or a sample of other substances.

After the collection 200, the sample is transferred as illustrated by arrow 202 for sample preparation 203. The sample preparation 203 provides an automated sample, an immunoassays sample, and/or a nucleic acid assays sample. In the sample preparation 203 the sample may be concentrated, purified, lisis of spores, mixed, and/or amplified.

After sample preparation 203, the sample is transferred as illustrated by arrow 204 for detection. In one embodiment of the autonomous pathogen detection system 200, the detection is by a multiplex immunoassay detector. In another embodiment of the autonomous pathogen detection system 200, the detection is by a multiplex PCR detector.

After sample preparation 203 and detection 205 when a pathogen has been detected, a sample is transferred from sample preparation 203 to the confirmation module 207. This is illustrated by arrow 206 in FIG. 2. In one embodiment, the system for confirmation of a bioagent in the sample is a multiplex immunoassay detector. In one embodiment of the autonomous pathogen detection system 200, the system for confirmation of a bioagent in the sample is a multiplex PCR detector. In one embodiment of the autonomous pathogen detection system 200, the system for confirmation of a bioagent in the sample is a real time PCR detector.

The autonomous pathogen detection system 200 provides an apparatus and method for monitoring air, water, soil, or other substance for particles containing bioagents. The autonomous pathogen detection system 200 comprises a collector for gathering the air, water, soil, or other substance being monitored; sample preparation means for preparing a sample from the air, water, soil, or other substance gathered by the collector; a detector for detecting a bioagents in the sample; and a system for confirmation of a bioagent in the sample. In one embodiment the collector is an aerosol collector. In other embodiments the collector gathers water, soil, or, other substances. The collector in one embodiment includes separator means for separating the particles of interest from other particles. The particles of interest are of a predetermined size range.

In one embodiment the collector is an aerosol collector that collects air and includes means for separating the air into a bypass air flow that does not contain the particles of a predetermined particle size range and a product air flow that does contain the sample particles of a predetermined particle size range. A wetted-wall cyclone collector receives the product air flow and traps and concentrates the particles of a predetermined particle size range in a liquid.

In one embodiment the sample preparation means is automated. In one embodiment the sample preparation means provides an immunoassays sample. In anther embodiment the sample preparation means provides a nucleic acid assays sample. In anther embodiment the sample preparation means provides the sample preparation means includes concentration of the air, water, soil, or other substance. In anther embodiment the sample preparation means provides the sample preparation means includes purification of the air, water, soil, or other substance. In anther embodiment the sample preparation means provides the sample preparation means includes lysis of the air, water, soil, or other substance. In anther embodiment the sample preparation means provides includes mixing of the air, water, soil, or other substance. In anther embodiment the sample preparation means provides includes amplification of the sample.

In one embodiment of the autonomous pathogen detection system 200, the detector 205 is a multiplex immunoassay detector. In one embodiment of the autonomous pathogen detection system 200, the detector 205 is a multiplex PCR detector.

In one embodiment of the autonomous pathogen detection system 200, the system 207 for confirmation of a bioagent in the sample is a multiplex immunoassay detector. In one embodiment of the autonomous pathogen detection system 200, the system 207 for confirmation of a bioagent in the sample is a multiplex PCR detector. In one embodiment of the autonomous pathogen detection system 200, the system 207 for confirmation of a bioagent in the sample is a real time PCR detector.

Referring now to FIG. 3 through FIG. 12 a specific embodiment of the invention designated as an AUTONOMOUS PATHOGEN DETECTION SYSTEM (APDS) is shown. The APDS is designated generally by the reference numeral 300. The APDS 300 integrates a flow cytometer and PCR detector with sample collection, sample preparation, and fluidics to provide a compact, autonomously operating instrument capable of simultaneously detecting multiple pathogens and/or toxins. The APDS 300 is designed for locations where it continuously monitors air samples and automatically reports the presence of specific biological agents. Plague and anthrax are two of the pathogens the APDS 300 identifies, along with a host of others. The APDS 300 includes the potential to measure up to 100 different agents and controls in a single sample.

The APDS 300 provides a stand-alone pathogen detection system capable of rapid, continuous, low cost environmental monitoring of multiple airborne biological threat agents. The system 300 provides a "Detect to Protect/Warn" system with a number of key properties. The system 300 is capable of detecting pathogens within a 1-2 hour time window, allowing for enough time to respond to an event. The system 300 is extremely low cost to maintain, since continuous monitoring is essential for many applications. The system 300 has sufficient sensitivity to cover a broad geographical area (limiting the necessary number of sensors) and has sufficient selectivity to virtually eliminate false positives.

Multiplexed assays are used to reduce reagent costs, making long term monitoring operations possible, for example in U.S. Postal Service mail screening. A orthogonal detection section combines antibody-based and nucleic acid-based assays and reduces false positives to a very low level. Antibody assays allow the detector to respond to all types of bioagents, including those without nucleic acids such as protein toxins. Nucleic acid assays allow much more sensitive detection, reducing the number of sensors needed to protect a given area. The fully autonomous aerosol collection and sample preparation capabilities limit maintenance requirements and makes integration into a central security or monitoring network possible.

Referring again to FIG. 3, a block diagram illustrates the APDS 300. In operation, an aerosol collector system continuously samples the air and traps particles in a swirling buffer solution. Particles of a given size distribution are selected by varying the flow rate across a virtual impactor unit. The in-line sample preparation system provides all sample preparation steps (i.e., mix, wash, incubation, etc.), and performs multiplex detection using a Luminex flow cytometer.

In the "detection" sub-system, a collected sample is mixed with optically encoded microbeads. Each color of microbead contains a capture assay that is specific for a given bioagent. Fluorescent labels are added to identify the presence of each agent on the bound bead. Each optically encoded and fluorescently labeled microbead is individually read in a flow cytometer, and fluorescent intensities are then correlated with bioagent concentrations.

In the "confirmation" sub-system, PCR (nucleic acid) amplification and detection confirms the presence of the bioagent. An archived sample is mixed with the Taqman reagent, and then introduced by a SIA system into a flow through polymerase chain reaction (PCR) system. Specific nucleic acid signatures associated with the targeted bioagent are amplified and detected using fluorescence generated from nucleic acid replication from the Taqman probes.

In the "Integrated Remote Control and Feedback" sub-system, a central computer uses a simple serial based Labview control system to control all instrument functions. A software system provides data acquisition, real time data analysis, and result reporting via a graphical user interface.

The APDS 300 is integrated into a self-contained "ATM" style chassis. All fluids and reagents are contained in the instrument. The ADPS 300 includes the following sub-systems: Aerosol Collection 301, In-Line Sample Preparation 302, Detection—Liquid-Array Based Multiplex Immunoassay Detection and/or Nucleic Assays Detection 303, Confirmation—In-Line Nucleic Acid Amplification and Detection 304, and Integrated Remote Control and Feedback 305. The subsystem will be described in greater detail.

APDS Aerosol Collection—301

The first stage of the APADS 300 is "aerosol collection" that provides collection of airborne particles that could contain targeted bioagents. Aerosol release of bioagents is considered one of the possible scenarios of a terrorist organization. One of the methods of rapidly exposing a large population to a biowarfare agent is through use of an aerosol (witness the effect of the recent, relatively small-scale anthrax mailroom releases). The aerosol collection system 301 continuously samples the air and traps particles in a swirling buffer solution. Particles of a given size distribution are selected by varying the flow rate across a virtual impactor unit.

The aerosol collection system 301 is a multi-stage aerosol collector that utilizes a low pass aerosol section and a virtual impactor preconcentration that delivers the particles of interest to a wetted wall cyclone collector. The virtual impactor captures particles 1-10 gm which is the size of particles most likely to be captured in the human lung. In the wetted wall cyclone collector, the particles are collected in a fluid, making downstream processing much easier. The fans and inputs to the obtain high collection rates, up to 3000 liters of air per minute flow through the detection system, allowing many particles to be collected over a short period. The aerosol collection system provides improved sensitivity and reduced collection times. An on board computer controls air flow rates and the size range of particles collected. A particle counter provides reaptime feedback on the size and quantity of particles collected.

Figure 5:
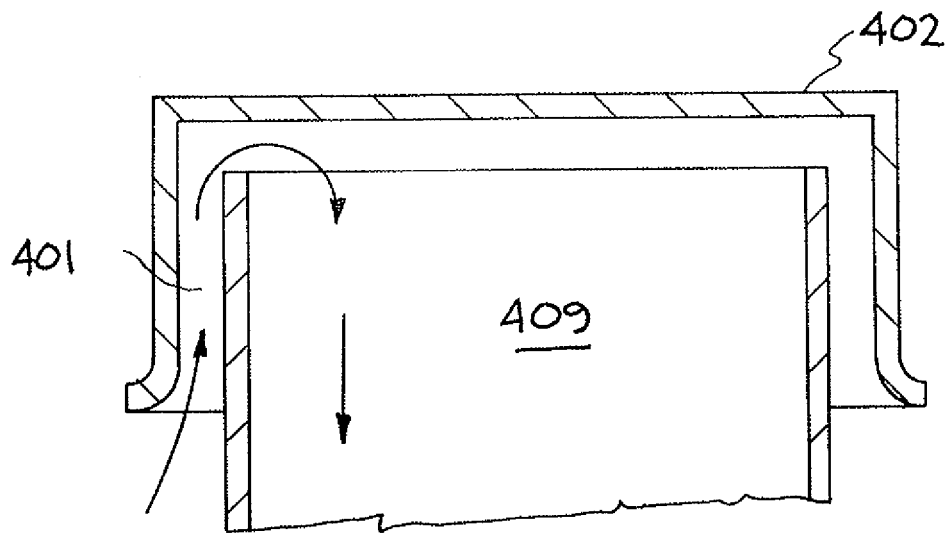
FIG. 5 is an illustration that shows the cap section limiting the larger particulate size range entering the collector.

As shown by FIGS. 4 and 5, a very high volume flow of aerosol particles is drawn into an annular slot 401 formed in a cap 402 that is designed to only allow the passage of particles smaller than a pre-set size. The pre-set size can be selected as desired. A very high volume flow of aerosol particles (e.g., up to 3313 Lpm) can be drawn into the annular slot 401 formed in the cap 402 that is designed to only allow the passage of particles smaller than 10 microns. The accepted particles continue on into a dichotomous virtual impaction section 403 that returns all the aerosol particles smaller than 1-micron back into the environment. The remaining particles, (1-10 microns) are known as the product, flow. The product flow continues into the next section.

As best illustrated by FIG. 5, a high volume flow of aerosol particles is drawn into the annular slot 401 formed in the cap 402. The annular slot 401 is designed to limit the upper or larger particulate size range as they enter the collector. To efficiently pass the smaller particulate, the cap 402 is a "passive" device in that is has no moving parts and uses the fact that particulate with a finite mass and moving in a flowstream (in this case air) will not follow the streamlines exactly due to their inertia. If the curvature of a streamline is sufficiently large and the mass of the particulate is correspondingly high, the particle deviates far enough from the streamline to impact with a surface. The particles are drawn into the annular slot 401 and directed into the transition section 409.

The APDS 300 has the capability to measure particle sizes in the sampling environment via a built in particle counter with four size ranges, and can store and display the results in real-time. The system is entirely self-contained requiring only a 110vac power connection. The on-board computer has high-speed communications capability allowing networks of these sampling systems to be remotely operated.

The APDS 300 is useful for most environmental sampling. It is particularly useful with biological material collection, but can be used for collecting any airborne matter. The APDS 300 can be used to sample air quality in public buildings such as convention centers and sports arenas, for sampling in food processing facilities, sampling animal pens (such as poultry houses), or for use in monitoring orchards or agricultural areas for the presence of pollens or pesticides. Because of it's relatively compact size and weight it can be used to sample in confined spaces such as found in aircraft or subway systems.

Figure 6:
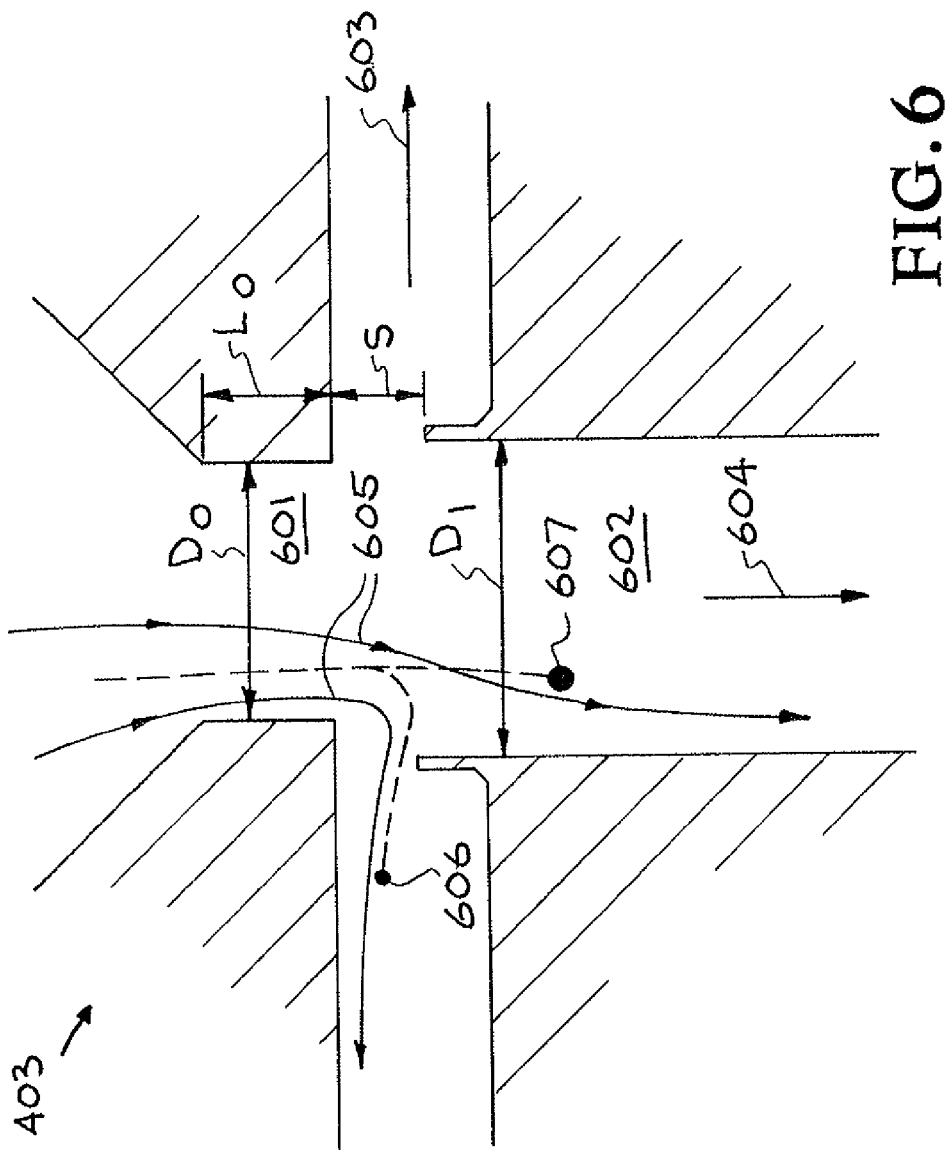
FIG. 6 is an illustration that shows the virtual impactor section.

Referring now to FIG. 6, the virtual impactor section 403 is shown in greater detail. In the virtual impactor section 403, the separation efficiency is determined by the ratio of the major and minor flows (or Bypass to Product) and the physical dimensions of the nozzle and collection probe. The key is particulate larger than the cut size become concentrated in the minor flow. The concentration factor is the ratio of the total flow to the minor flow. (If the minor flow is 25% of the total flow, then the concentration factor is 4.) The aerosol passes through an acceleration nozzle 601. The acceleration nozzle 601 has a diameter $D_0$. The aerosol is directed toward a collection probe 602. The collection probe has a diameter $D_1$. Between the acceleration nozzle 601 and the collection probe 602, a major portion of the flow 603 is diverted 90° away. The minor or "product" flow 604 continues axially.

The flow forms streamlines 605. Small particles with low inertia 606 follow the flow streamlines and are carried away radially with the major flow 603. Large particles with greater inertia 607 deviate from the flowlines but they continue moving axially in their forward path down the collection probe 602 with the minor or "product" flow 604. The separation efficiency is determined by the ratio of the major and minor flows (or Bypass to Product) and the physical dimensions of the nozzle $D_0$ and collection probe $D_1$. The key is particulate larger than the cut size become concentrated in the minor flow. The concentration factor is the ratio of the total flow to the minor flow.

Figure 7:
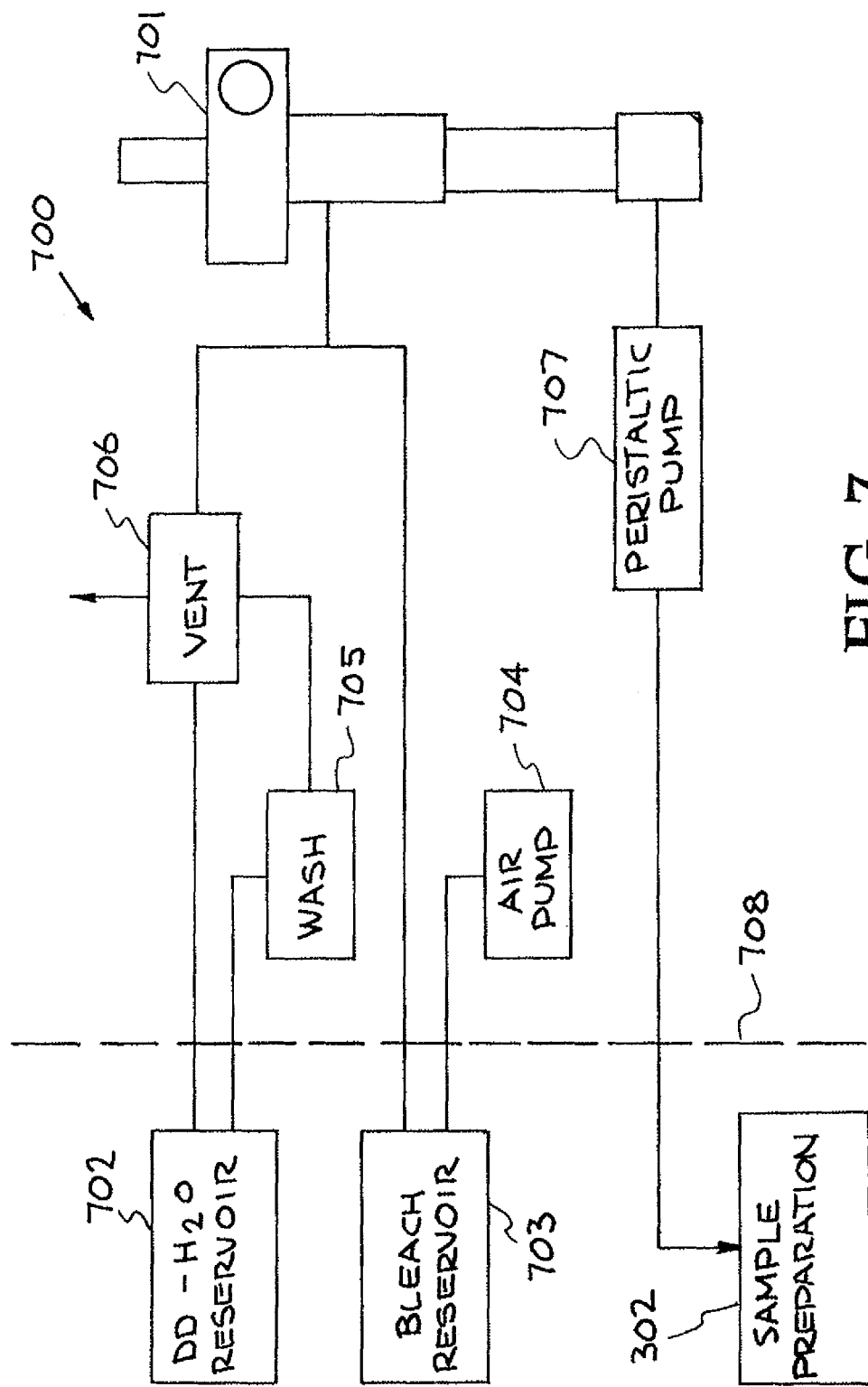
FIG. 7 shows the multistage, wetted-wall cyclone collector section.

Referring now to FIG. 7, additional details of the sample collection operation are shown. The particles, (1-10 microns) known as the product flow are directed into a multi-stage, wetted-wall cyclone collection section. In this stage of the sampling system the product particles are trapped and concentrated into a liquid, typically water, in a volume between 2 and 7 cc. An on-board computer monitors and controls the flow of air through the system using built in hot wire anemometers, as well as controlling the liquid level in the cyclone. At a selected time the computer will stop the flow of air and turn on a built-in peristaltic pump to deliver the sample via an external liquid sample port.

The product flow particles enter a stainless steel funnel section into the input of a multistage, wetted-wall cyclone collector section 700. The system includes a cyclone collector 701, peristaltic pump 707, an air pump 704, a vent 706, wash 705, 8 liter DD-$H^2O$ reservoir 702, and 1 liter bleach reservoir 703. The reservoirs 702 and 703 are provided as external tanks outside of the front panel interface 708. The multistage, wetted-wall cyclone collector section 700 directs the particles of interest to the sample preparation system 302.

The on-board computer monitors and controls the flow of air through the system using built in hot wire anemometers that have been mounted in the two exhaust ports of the sampler. The computer and control software also act to control the liquid level in the cyclone, and monitor all status indicators of the sampling system. At a selected time the computer will stop the flow of air and turn on a built-in peristaltic pump to deliver the collected liquid sample via an external sample port. The system also has the capability to measure particle sizes in the background environment via a built in particle counter such as particle counter Biotest APC-1000, with four size ranges, and can store and display the results in real-time.

The system 300 is entirely self-contained requiring only a 110vac power connection. The on-board computer has high-speed communications capability allowing networking of multiple sampling systems to be remotely operated. The computer has extra RS-232 or RS-485 serial ports that can be used to control other instrumentation. A keyboard, mouse, printer, displays, and other peripherals can be "plugged" in at the rear of the system, or it can be started "headless" (headless=Without a display, mouse, etc.)

Figure 8A:
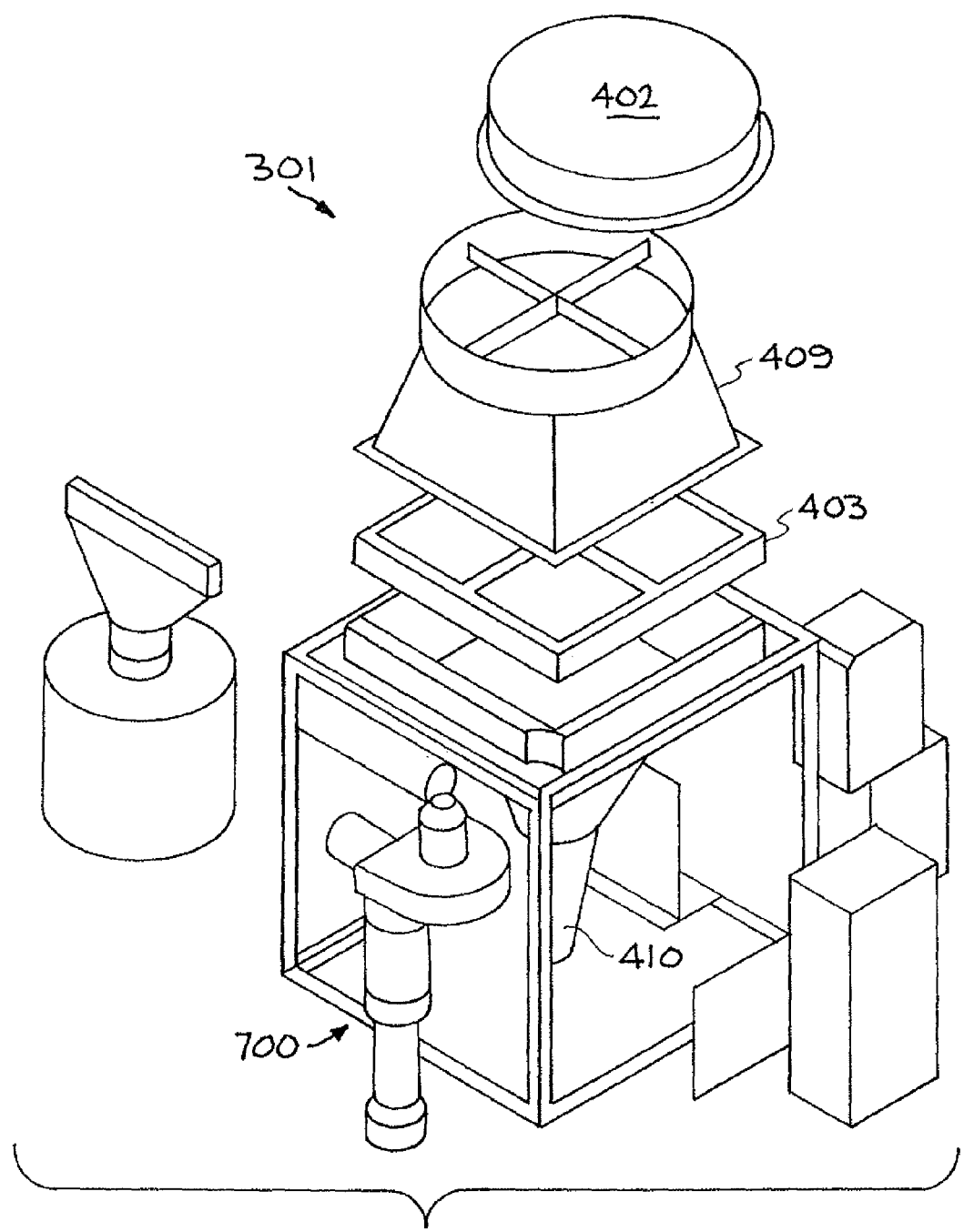
FIGS. 8A, 8B, and 8C show details of a specific embodiment of the aerosol collection system.
Figure 8C:
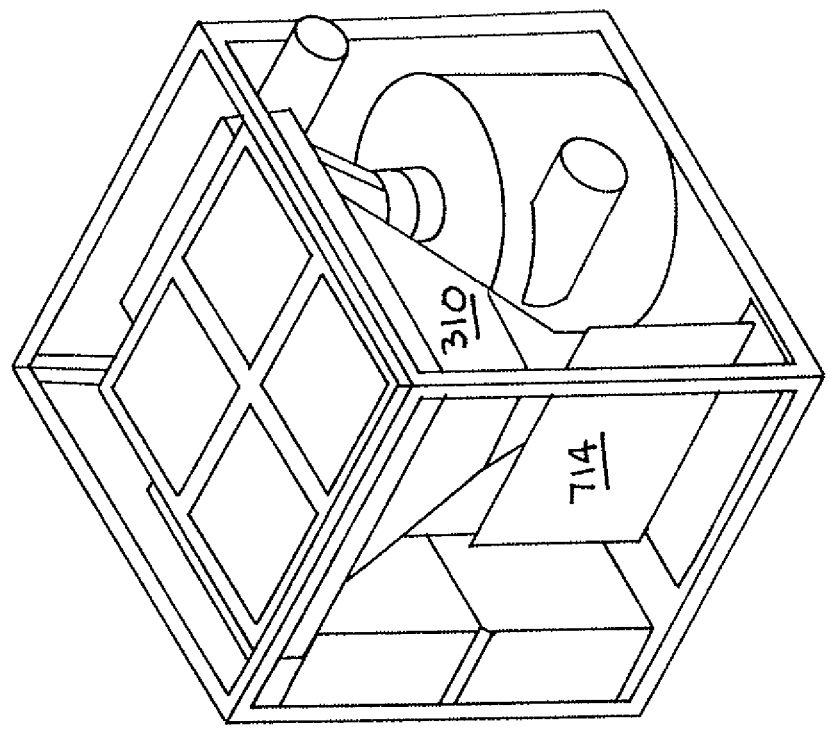
Figure 8B:
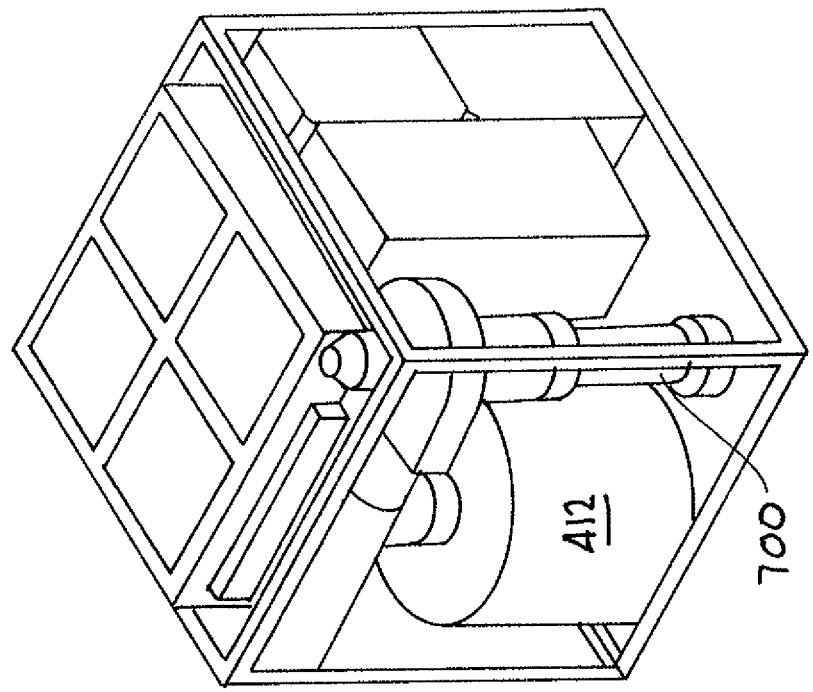

Referring now to FIGS. 8A, 8B, and 8C, the APDS Aerosol Collection 301 and APDS In-Line Sample Preparation 302 sub systems are shown in greater detail. The aerosol collection system 301 is designated "High Collection Rate Aerosol Sampling System" (HiCRASS). The HiCRASS comprises: Low Pass "Cap" 402; Transition Section 409; Virtual Impactor 403; Funnel Section 410; Multistage, Wetted-wall Cyclone Collector 700; Bypass Fan 412; and Control Computer 714.

The HiCRASS system provides a very high volume flow of aerosol particles (e.g., up to 3313 Lpm) that are drawn into the annular slot 401 formed in the cap 402 that is designed to limit the upper or larger particulate size range as they enter the collector. The annular slot 401 allows the passage of particles smaller than 10 microns. To efficiently pass the smaller particulate, the cap 402 is a "passive" device in that is has no moving parts and uses the fact that particulate with a finite mass and moving in a flowstream (in this case air) will not follow the streamlines exactly due to their inertia. The curvature of the streamline is sufficiently large and the mass of the particulate is correspondingly high that the particle deviates far enough from the streamline to impact with a surface. The accepted particles continue around the corner and onto the dichotomous virtual impaction section 403 that returns substantially all the aerosol particles smaller than 1-micron back into the environment.

The virtual impactor 403 works as the aerosol passes through an accelerating nozzle 601 and is directed toward a collection probe 602 where a major portion of the flow 603 is diverted 90° away from it. The flow forms streamlines 605. Small particles with low inertia 606 follow the flow streamlines and are carried away radially with the major flow 603. Large particles with greater inertia 607 deviate from the flowlines but they continue moving axially in their forward path down the collection probe 602 with the minor or "product" flow 604. The separation efficiency is determined by the ratio of the major and minor flows (or Bypass to Product) and the physical dimensions of the nozzle $D_0$ and collection probe $D_1$. Particulate larger than the cut size become concentrated in the minor flow. The concentration factor is the ratio of the total flow to the minor flow. (If the minor flow is 25% of the total flow, then the concentration factor is 4).

The remaining particles (1-10 microns) now known as the product 604, flow down a stainless steel funnel section into the input of the multistage, wetted-wall cyclone collector section 700. In this stage of the system 301 the product particles are trapped and concentrated into a liquid, typically water, in a volume between 2 and 7 cc. The wetted-wall cyclone collector section 700 is a system that causes the product flow particles 604 to be collected by a liquid. The wetted-wall cyclone collector section 700 operates by forcing the air stream tangentially into a cylinder causing the air stream to circulate around the inside of the cylinder. Particles in the air stream having sufficient inertia will collide with the interior wall where they are collected by the liquid that circulates along the interior wall.

The on-board computer 714 monitors and controls the flow of air through the system using built-in hot wire anemometers, as well as controlling the liquid level in the cyclone 700. At a selected time the computer 714 will stop the flow of air and turn on a built-in peristaltic pump to deliver the sample via an external sample port. The on-board computer 714 monitors and controls the flow of air through the system using built in hot wire anemometers that have been mounted in the two exhaust ports of the sampler. The computer and control software also act to control the liquid level in the cyclone, and monitor all status indicators of the sampling system. At a selected time the computer will stop the flow of air and turn on a built-in peristaltic pump to deliver the collected liquid sample via an external sample port.

The system also has the capability to measure particle sizes in the sampling environment via a built in particle counter such as particle counter Biotest APC-1000, with four size ranges, and can store and display the results in real-time. The syste is entirely self-contained requiring only a 110vac power connection. The on-board computer has high-speed communications capability allowing networks of these sampling systems to be remotely operated.

Figure 9:
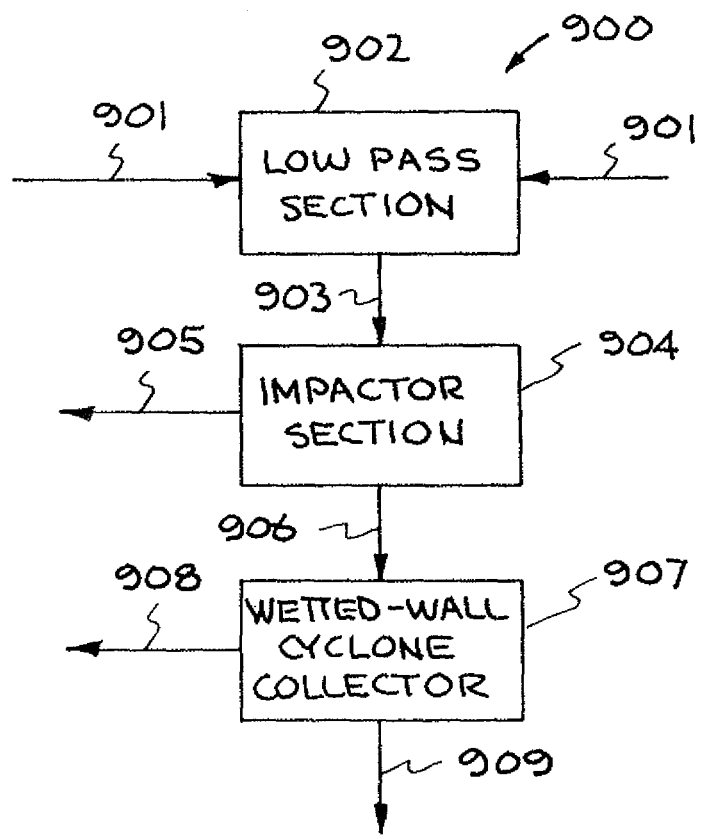
FIG. 9 is an illustration that shows another embodiment of the aerosol collection system.

Referring now to FIG. 9, another embodiment of the collection section of the present invention is illustrated. This collection section system is designated generally by the reference numeral 900. The system 900 samples the air 901 and collects sample particles of a predetermined particle size range from the air. The system 900 is particularly useful with the latest generation of Biological Warfare agent detection systems. An air sampling system is a critical component in integrated biological warfare detection system. The system 900 also has use in medical facilities and research and development facilities.

A low pass section 902 has an opening of a preselected size for gathering the air 901 but excluding particles larger than the sample particles. In one embodiment, the opening of a preselected size is an annular slot that only allows the passage of particles smaller than 10 microns. The low pass section 902 produces a total air flow 903 that contains the sample particles of a predetermined particle size range. The low pass section 902 allows a very high volume flow of air to be drawn through the preselected size opening. In one embodiment, the very high volume flow of air is 3313 Lpm or less.

An impactor section 904 is connected to the low pass section 902 and receives the total air flow 903. The impactor section 904 separating the total air flow 903 into a bypass air flow 905 that does not contain the sample particles and a product air flow 906 that does contain the sample particles. An accelerating nozzle and a collection probe in the impactor section 904 diverts the bypass air flow 90° from the product air flow thereby separating the bypass air flow and the product air flow. In one embodiment, the bypass air flow and the product air flow separation is determined by the ratio of the bypass air flow and the product air flow. In one embodiment, the bypass air flow and the product air flow separation is determined by the physical dimensions of the accelerating nozzle and the collection probe. In one embodiment, the bypass air flow and the product air flow separation is determined by the ratio of the bypass air flow and the product air flow and the physical dimensions of the accelerating nozzle and the collection probe.

A wetted-wall cyclone collector section 907 is connected to the impactor section 904. The wetted-wall cyclone collector section 907 receives the product air flow 906 and traps the sample particles in a liquid. The sample particles of a predetermined particle size range are concentrated in the liquid. In one embodiment, the wetted-wall cyclone collector section 907 traps and concentrates the sample particles into a liquid in a volume between 2 and 7 cc. In one embodiment, the liquid is water.

The system 900 is useful for most environmental sampling. It is particularly useful with biological material collection, but can be used for collecting any airborne matter. The system 900 can be used to sample air quality in public buildings such as convention centers and sports arenas, for sampling in food processing facilities, sampling animal pens (such as poultry houses), or for use in monitoring orchards or agricultural areas for the presence of pollens or pesticides. Because of its relatively compact size and weight it can be used to sample in confined spaces such as found in aircraft or subway systems.

APDS In-Line Sample Preparation—302

As best illustrated in FIG. 3, the in-line sample preparation module 302 moves the sample from the aerosol collection module 301 to appropriate modules within the APDS 300 and provides sample preparation. In one mode, the sample preparation module 302 prepares the sample (mixing, filtering, incubation, etc.) and delivers the sample reaction volume to the liquid-array based multiplex immunoassay detection system 303. In another mode, the sample preparation module 302 prepares the sample (mixing, filtering, incubation, etc.) and delivers the sample reaction volume to the in-line nucleic acid detection system 304.

The prior art sample preparation instrumentation uses robotic manipulation of micropipettes coupled to disposable filter wells. Robotics are inherently complex and difficult to scale. The sample preparation module 302 uses Zone fluidics. Zone fluidics is the precisely controlled physical, chemical, and fluid-dynamic manipulation of zones of miscible and immiscible fluids in narrow bore conduits to accomplish sample conditioning and chemical analysis. A zone is a volume region within a flow conduit containing at least one unique characteristic. A unit operation in zone fluidics comprises of a set of fluid handling steps intended to contribute to the transformation of the sample into a detectable species or prepare it for manipulation in subsequent unit operations. Examples of unit operations include sample filtering, dilution, enrichment, medium exchange, headspace sampling, solvent extraction, matrix elimination, de-bubbling, amplifying, hybridizing, and reacting. In current analytical practice many of these steps are handled manually or in isolated pieces of equipment. Integration is scant at best, and there is a high degree of analyst involvement. In zone fluidics, sample and reagent zones are subjected to these unit operations in a sequential manner being transported from one unit operation to the next under fluidic control.

Samples in zone fluidics are not limited to liquids. Rather, gases, and suspensions containing solids or cells are also included. Where solid samples are used, particles are limited to a size that ensures no blockages. In most cases, reagents are prepared and then coupled to the zone fluidics manifold. The metering capability of the pump and mixing unit operations allow for reagents and standards to be prepared in situ. Reagents can therefore be presented to the zone fluidics manifold in an appropriately designed cartridge as ready-made, reagent concentrates, lyophilized, or crystalline form. Standards can be plumbed to the multi-position valve as discrete reservoirs providing the required range of concentrations. As for reagents though, standards can also be prepared in situ or diluted to cover a larger dynamic range.

The sample preparation module 302 uses a powerful, highly flexible technique called sequential injection analysis (SIA). Automation is achieved through the manipulation of small solution zones under conditions of controlled dispersion in narrow bore tubing. Zone fluidics makes use of a mufti-position selection valve and a high precision, bi-directional pump to construct a stack of well-defined sample and reagent zones in a holding coil of narrow bore tubing. By appropriate manipulation of this zone stack, a wide range of sample handling unit operations can be accommodated. The pump is used to move the sample from one device to the next achieving the required sample manipulation in the process. Once a detectable species has been formed, the zone stack is transported to the immunoassay detector 303 and to the nucleic acid detector 304.

Figure 10:
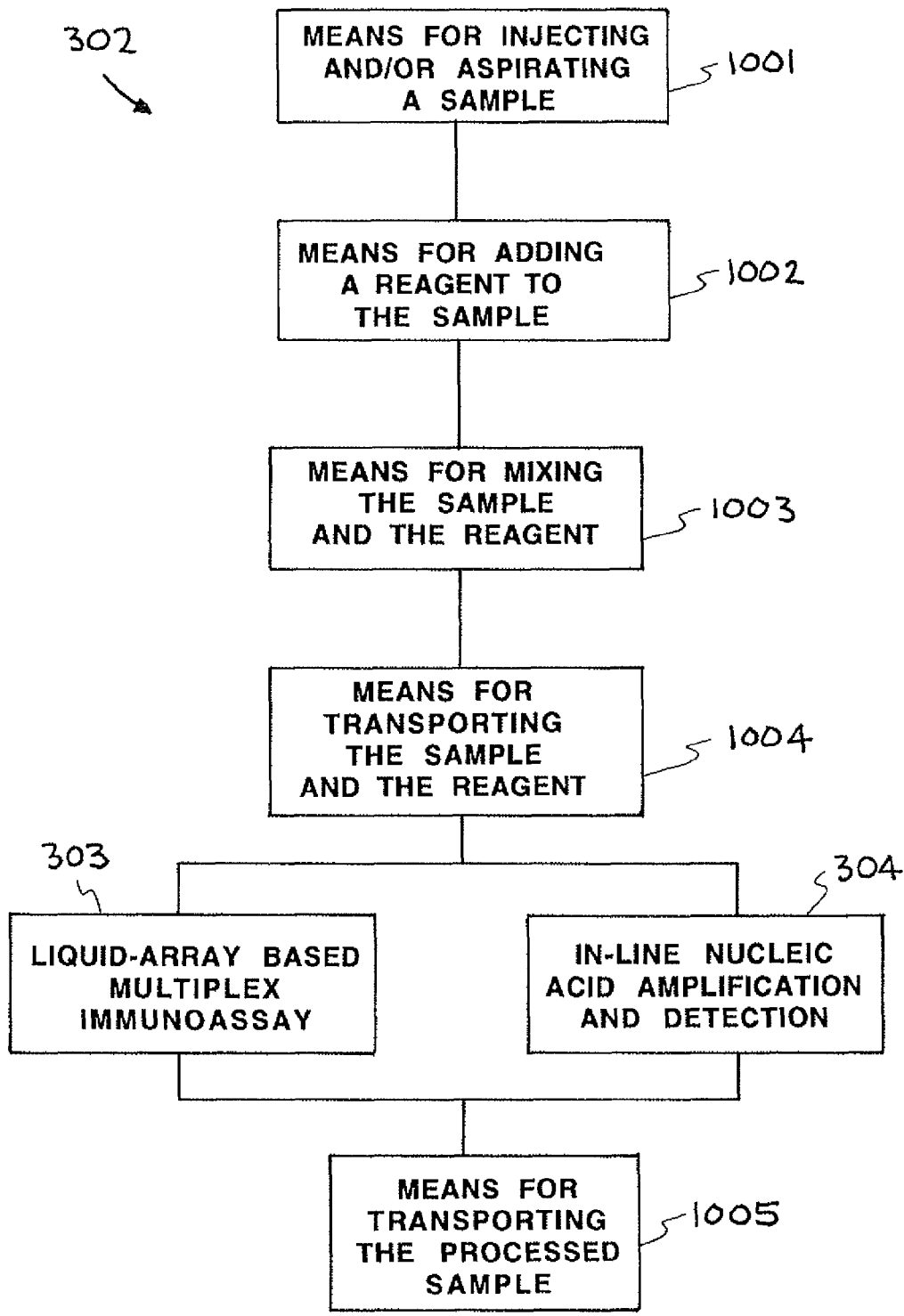
FIG. 10 illustrates a system for sample preparation and detection.

Referring now to FIG. 10, a system for sample preparation and detection is illustrated. The system is generally designated by the reference numeral 302. The In-Line Sample Preparation 302 is capable of performing, singly or in combination, Liquid-Array Based Multiplex Immunoassay Detection 303 and/or In-Line Nucleic Acid Amplification and Detection 304. The In-Line Sample Preparation module 302 includes various components described below.

A means for injecting and or aspirating a sample 1001 provides injection and/or aspiration of the sample. In one embodiment the injecting/aspirating means 1001 consists of a zone fluidics system. In another embodiment the injecting/aspirating means 1001 consists of an FIA system. The means 1001 for injecting and or aspirating a sample can be, for example, a injecting/aspirating device available under the trademark milliGAT™ pump, Global FIA, Inc, Fox Island, Wash.

A means for adding a reagent to the sample 1002 is operatively connected to the means 1001 for injecting and or aspirating a sample. The means for adding reagent to the sample 1002 can be, for example, a unit for adding reagent to the sample such as an injection or multi position selection valve, available from VICI, Houston, Tex.

A means for mixing the sample and the reagent 1003 is operatively connected to the means for adding reagent to the sample 1002. The mixing means 1003 mixes the sample with a reagent. The means 1003 for mixing the sample and the reagent can be, for example, a super serpentine reactor, available from Global FIA, Inc, Fox Island, Wash.

A means for transporting the sample and the reagent 1004 is operatively connected to the means for mixing the sample and the reagent 1003. The means for transporting the sample and the reagent 1004 consists of a fluidics system. The means for transporting the sample and the reagent 1004 can be, for example, FEP tubing available from Cole-Parmer, Vernon Hills, Ill.

The Liquid-Array Based Multiplex Immunoassay Detection module 303 measures a multiple pathogen targets in the sample. The Liquid-Array Based Multiplex Immunoassay Detection module 303 will be described in detail subsequently.

The In-Line Nucleic Acid Amplification and Detection module 304 provides a second detection system that is based on nucleic acid amplification and detection. The In-Line Nucleic Acid Amplification and Detection module 304 can be, for example, a detection system described in publications and products produced by Cepheid and Baltimore-based Environmental Technologies Group, Inc. (ETG), a part of London-based Smiths Aerospace. The In-Line Nucleic Acid Amplification and Detection module 304 will be described in detail subsequently.

A means 1005 for transporting the amplified sample from the Liquid-Array Based Multiplex Immunoassay Detection module 303 and the In-Line Nucleic Acid Amplification and Detection module 304. The means 1005 for transporting the amplified sample from the PCR reactor can be, for example, BEP tubing available from Cole-Parmer, Vernon Hills, Ill.

Conduits are included within the sample preparation module 302, Decontamination and conditioning the conduits is accomplished by flushing the conduits with a suitable fluid. For example, the decontamination and conditioning of all exposed conduits can be performed by using a decontaminant, such as bleach, which is pumped through the exposed conduits and then washed from the system with a suitable wash solution.

The integrated remote control and feedback module 305 is inherently autonomous, meaning control and/or monitoring functions are ideally performed remotely. This networking of sensors can occur in multiple different ways, from wireless solutions using RF, to conventional hard-wired internet connections. Integrated remote control and feedback module 305 is setup as a network of multiple units to protect large areas, the higher sensitivity lowers the number of required units. This reduces reagent and other associated costs making deployment more feasible for a larger number of public events. The integrated remote control and feedback module 305 is statistically analyzed with a 1,000-sample aerosol sample library. This library has been prescreened for the same pathogenic agents used in the multiplex signatures. Therefore, any detection events will serve as a final screen for incompatible primer pairing.

Detection—APDS Liquid-Array Based Multiplex Immunoassay Detection—303

In operation of the APDS system 300, the aerosol collector system samples the air, particles of a given size distribution are trapped in a liquid, and a sample of interest is prepared. The next step is detection of any pathogens in the sample particles. The Liquid-Array Based Multiplex Immunoassay Detection system 303 measures a multiple pathogen targets in the sample. The Liquid-Array Based Multiplex Immunoassay Detection system 303 has the ability to use a detection modality that measures multiple pathogen targets in the same sample. This prevents loss of sensitivity due to sample dilution and severely reduces the recurring assay cost for the instrument. "Liquid arrays" allow optical or physical (i.e., shape, magnetism, etc.) encoding of particles that then form the template for performing assays. In one embodiment of the invention the Liquid-Array Based Multiplex Immunoassay Detection system 303 uses Luminex technology. In other embodiments, nanobarcodes—rod shaped structures on the nanometer scale that can be optically barcoded with metal strips and then measured via reflectance; quantum dots—encapsulation of nanometer scale particles that emit specific light over a broad spectral range; and upconverting phosphers are used. The liquid array detection can occur as a preliminary screen, since it has the capability to detect all types of pathogens (viruses, bacteria, proteins, and spores) and is relatively low cost.

The Liquid-Array Based Multiplex Immunoassay Detection system 303 uses a "liquid arrays," a highly multiplexed assay that competes (in bead format) with "computer chip" platforms. In the APDS system 300, the Liquid-Array Based Multiplex Immunoassay Detection system 303 uses Luminex technology from Luminex Corporation, Austin, Tex. The detection principle is built around the use of optically encoded microbeads that can be used as assay templates. Small diameter polystyrene beads are coded with 1000s of antibodies. The sample is first exposed to the beads and the bioagent, if present, is bound to the bead. A second, fluorescently labeled antibody is then added to the sample resulting in a highly fluorescent target for flow analysis. Since the assay is performed on a microbead matrix, it is possible to measure all types of pathogens, including viruses and toxins. Each microbead is colored with a unique combination of red and orange emitting dyes. The number of agents that can be detected from a single sample is limited only by the number of colored bead sets. The system includes the following components: microbead specific reagents, incubation/mixing chambers, a microbead capture array, and an optical measurement and decoding system.

The Liquid-Array Based Multiplex Immunoassay Detection system 303 has sufficient precision to make a 10×10 array of beads, making 100-plex bioagent detection viable. This can measure a wide range of bioagents at sensitivities and selectivities comparable to non-automated conventional immunoassay techniques (such as enzyme-linked immunosorbent assays) that take 4-6 times as long. Additional bead types are used as internal positive and negative controls to monitor each step in the sample preparation process. This provides quality control.

Confirmation—APDS In-Line Nucleic Acid Amplification and Detection—304

In operation of the APDS system 300, the aerosol collector system has sampled the air, particles of a given size distribution have been trapped in a liquid, a sample of interest has been prepared, and the detection system has detected a pathogen in the sample. The next step is confirmation of the pathogen that has been detected in the sample. The in-line nucleic acid amplification and detection system 304, confirms the pathogen that has been detected in the sample. PCR amplification devices are described in publications such as U.S. Pat. No. 5,589,136 for silicon-based sleeve devices for chemical reactions, assigned to the Regents of the University of California, inventors: M. Allen Northrup, Raymond P. Mariella, Jr., Anthony V. Carrano, and Joseph W. Balch, patented Dec. 31, 1996 and many are commercially available such as ABI PRISM® 7700 Sequence Detection System by Applied Biosystems; iCycler iQ Real-Time PCR Detection System by Bio-Rad; and Smart Cycler® System by Cepheid.

Referring now to FIGS. 11, 12, and 13, the liquid-array based multiplex immunoassay detection system 303 is illustrated in greater detail. FIG. 11 shows a 100-plex Luminex bead set 1100 generated by intercalating varying ratios of red and orange dyes into polystyrene latex microspheres 1101. Each optically encoded bead 1101 has a unique spectral address. The beads 1101 are shown arranged so that they increase in red intensity in the vertical axis and increase in orange intensity in the horizontal axis providing the unique spectral address.

FIG. 12 shows the beads 1101 coated with capture antibodies specific for target antigens. Examples of capture antibodies include, anthrax 1102, plague 1103, small pox 1104, and botox 1105. After incubating with the antigens, secondary or detector antibodies are added, followed by addition of the fluorescent reporter, phycoerythrin to complete the "antigen sandwich."

FIG. 13 shows the beads 1101 being analyzed in a flow cytometer 1106. The beads 11-1 are interrogated one at a time. A red laser 1107 (red) classifies the bead, identifying the bead type. A green laser 1107 (green) quantifies the assay on the bead surface, only those beads with a complete sandwich will fluoresce in the green, and the signal is a function of antigen concentration.

Referring again to FIG. 11, a set of 100 polystyrene microbeads 1101 is shown. The beads are imbedded with precise ratios of red and orange fluorescent dyes yielding an array of one hundred beads, each with a unique spectral address. Each bead 1101 is coated with capture antibodies specific for a given antigen as illustrated in FIG. 12. After incubating with the antigens, secondary or detector antibodies are added, followed by addition of the fluorescent reporter, phycoerythrin to complete the "antigen sandwich."

After antigen capture, secondary antibodies sandwich the bound antigen and are indirectly labeled by the fluorescent reporter phycoerythrin (PE). Referring again to FIG. 13, each optically encoded and fluorescently-labeled microbead is individually interrogated by a Luminex flow cytometer 1106. A red laser 1107 (red) excites the dye molecules imbedded inside the bead and classifies the bead to its unique bead set, and a green laser 1107 (green) quantifies the assay at the bead surface. The flow cytometer is capable of reading thousands of beads each second; analysis can be completed in a little as 15 seconds.

Microbeads have several advantages over other solid-phase supports such as planar waveguides or microtiter wells. First, the 5.5 (±0.1) μm spheres provide a large surface area that can accommodate up to 100,000 capture antibodies per bead. The high density of capture antibodies ensures maximum antigen binding, thereby enhancing assay sensitivity. Second, because beads are freely suspended in solution, the entire surface area is exposed, increasing the probability of collisions with antigen in the proper orientation for binding, facilitating rapid reactions. Agitating or heating the reaction volume further improves reaction kinetics. Also, the beads are effectively filtered on a filter-bottomed plate. Filtration allows unbound antigen and other excess reagents to be washed away, minimizing both non-specific binding and undesired increases in background fluorescence.

Figure 11:
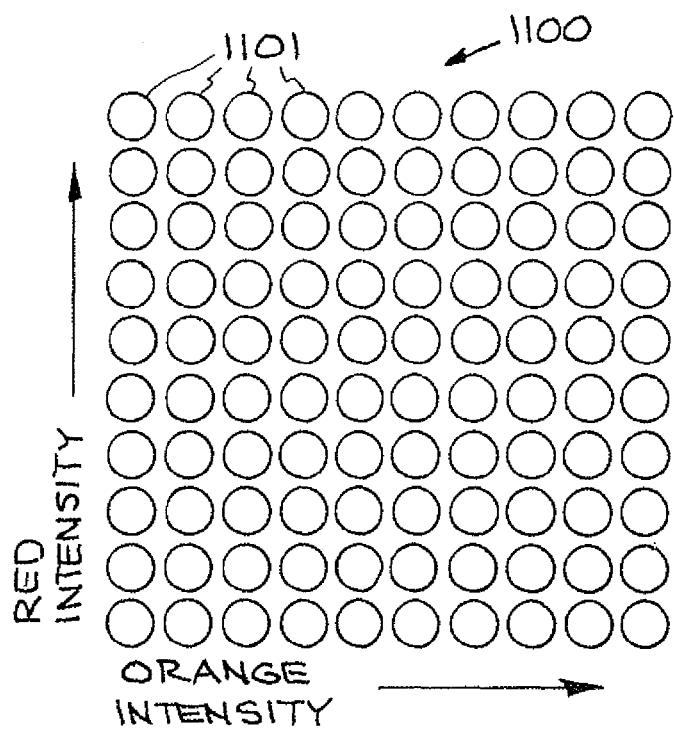
FIGS. 11, 12, and 13 illustrate the liquid-array based multiplex immunoassay detection system.
Figure 13:
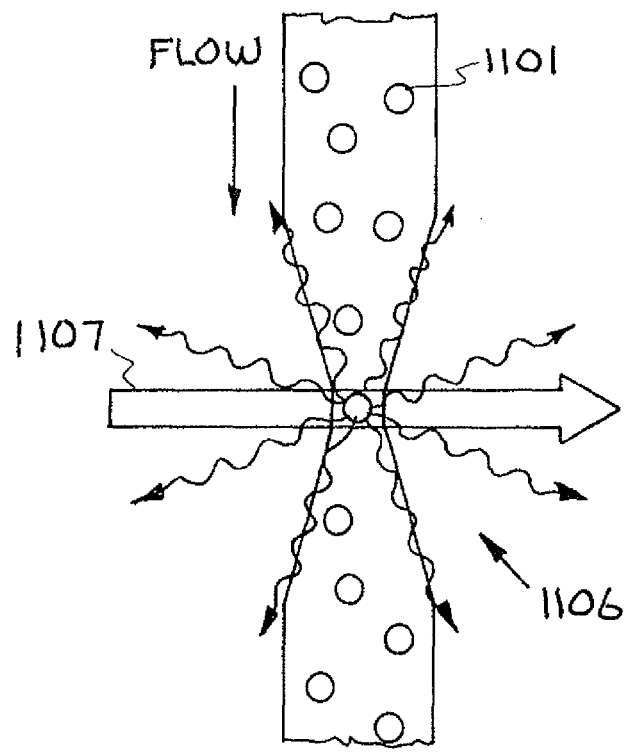
Figure 12:
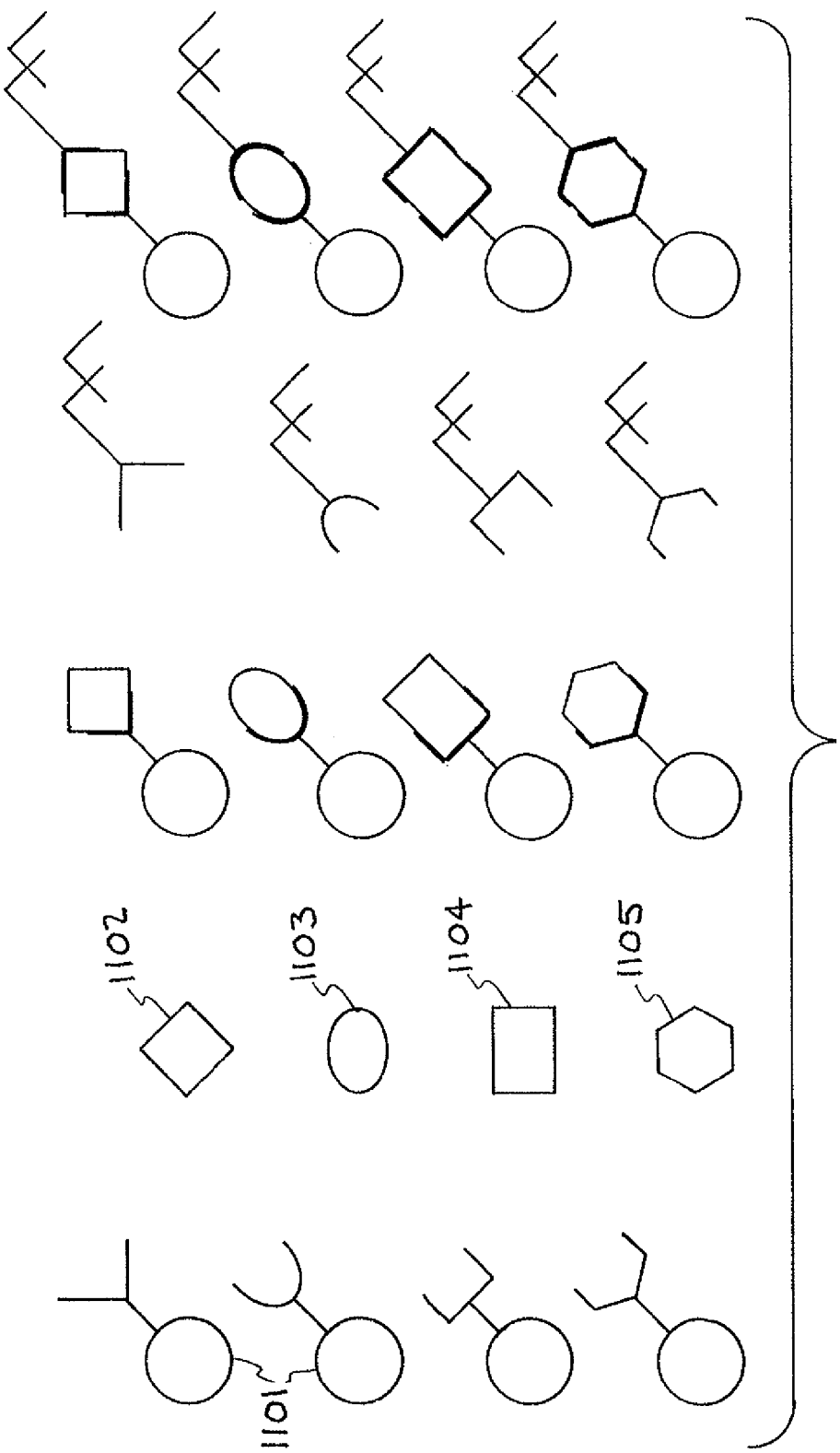

The liquid-array based multiplex immunoassay detection system 303 illustrated in FIGS. 11, 12, and 13 measures multiple pathogen targets in the sample. Up to 100 different pathogens can be detected in a single assay. Different antibodies on each bead enables highly multiplex detection. Luminex bead-based assays that are truly multiplexed; that is, assays designed for the simultaneous detection of multiple threat agents using a single sample. An example of a liquid-array based multiplex immunoassay detection system is shown in U.S. Patent Application 2003/0003441 by Billy W. Colston, Matthew Everett, Fred P. Milanovich, Steve B Brown, Kodumudi Venkateswaran, and Jonathan N. Simon, published Jan. 2, 2003. The disclosure of U.S. Patent Application 2003/0003441 is incorporated herein by reference.

Figure 14:
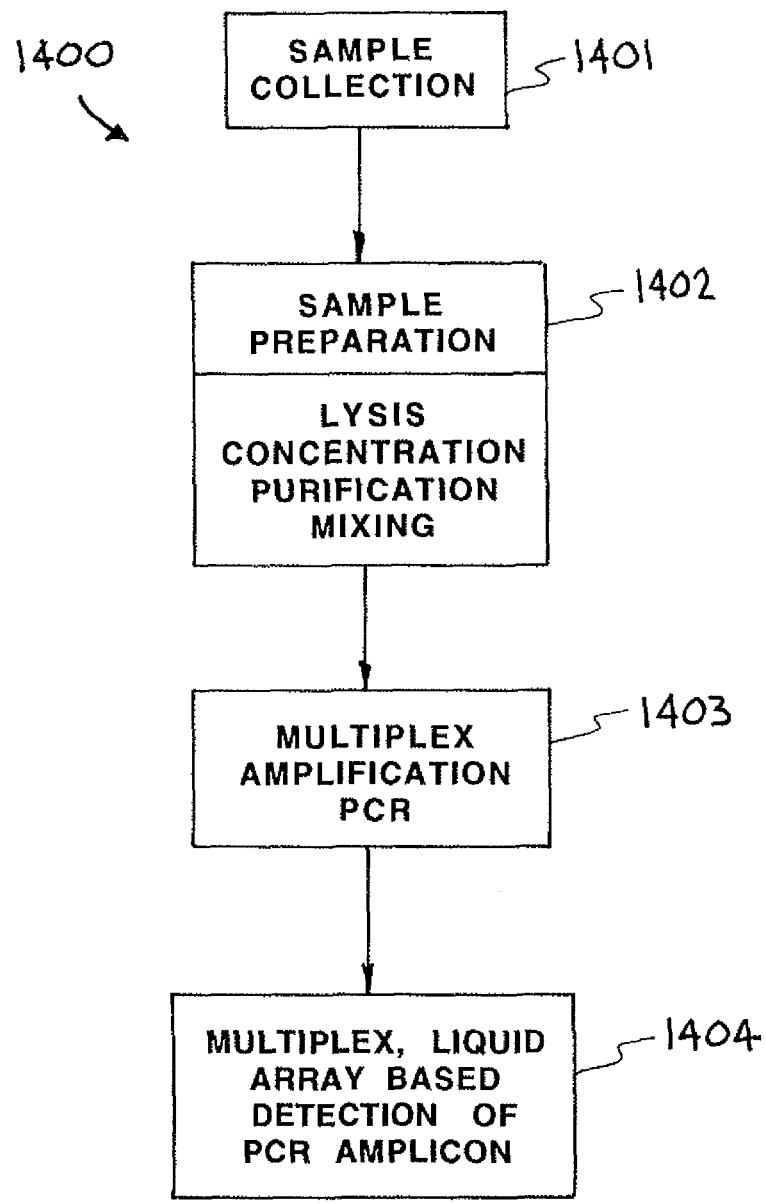
FIG. 14 is a block diagram illustrating the multiples amplification and detection system.

Referring now to FIG. 14, another embodiment of a system constructed in accordance with the present invention is illustrated. The system is designated generally by the reference numeral 1400. The system 1400 comprises the following: Sample Collection 1401, Sample Preparation 1402, Multiplex Amplification PCR 1403, and Multiplex, Liquid Array Based Detection of PCR Amplicon 1404.

The first stage of the system 1400 is "sample collection 1401" that provides collection of particles that could contain targeted bioagents. The sample collection 1401 gathers air, water, soil, or other substance being monitored. The sample collection 1401 separates selected potential bioagent particles from the air, water, soil, or other substance.

The "sample preparation 1402" moves the sample from the sample collection to appropriate modules within the system 1400 and provides sample preparation. In one mode, the sample preparation 1402 prepares the sample (Lysis, Concentration, Purification, Mixing, etc.) and delivers the sample to "Multiplex Amplification PCR 1403." One mode provides "Multiplex, Liquid Array Based Detection of PCR Amplicon 1404." An example of a flow cytometric detection method for DNA samples is shown in U.S. Patent Application 2002/0155482 by Shanavaz Nasarabadi, Richard G. Langlois, and Kodumudi Venkateswaran published Oct. 24, 2002. The disclosure of U.S. Patent Application 2002/0155482 is incorporated herein by reference.

Figure 15:
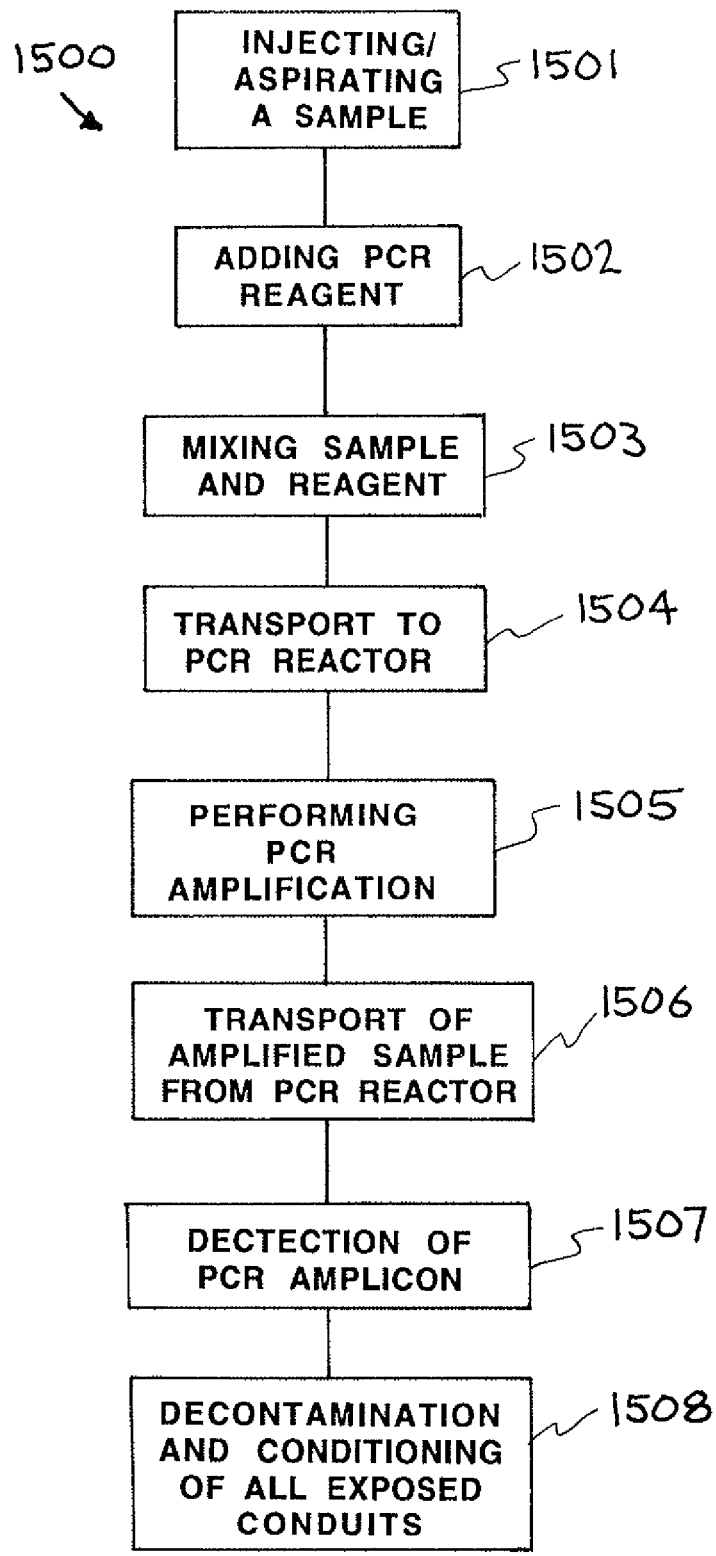
FIG. 15 illustrates one specific embodiment of the in-line nucleic acid amplification and detection system.

Referring now to FIG. 15, one specific embodiment of the in-line nucleic acid amplification and detection system 1500 is illustrated. The system 1500 is capable of performing, singly or in combination, nucleic acid amplification, and nucleic acid detection functions. The nucleic acid assay system 1500 includes a number of components including means for injecting/aspirating a sample, 1501, means for adding PCR reagent 1502, means for mixing sample and reagent 1503, means for transport to PCR reactor 1504, means for performing PCR amplification 1505, means for transport of amplified sample from PCR reactor 1506, means for detection of PCR amplicon 1507, and means for decontamination and conditioning of all exposed conduits 1508.

The means 1501 for injecting and or aspirating a sample provides injection and/or aspiration of the sample. In one embodiment the injecting/aspirating means 1501 consists of a zone fluidics system. In another embodiment the injecting/aspirating means 1501 consists of an FIA system. The means 1501 for injecting and or aspirating a sample can be, for example, a injecting/aspirating device available under the trademark milliGAT™ pump, Global FIA, Inc, Fox Island, Wash.

The means 1502 for adding PCR reagent to the sample is operatively connected to the means 1501 for injecting and or aspirating a sample. The means 1502 for adding PCR reagent to the sample can be, for example, a unit for adding PCR reagent to the sample such as an injection or multi position selection valve, available from VICI, Houston, Tex.

The means 1503 for mixing the sample and the reagent is operatively connected to the means 1502 for adding PCR reagent to the sample. The mixing means 1503 mixes the sample with a PCR reagent. In one embodiment the PCR reagent includes primers. In another embodiment the PCR reagent includes oligos. The means 1503 for mixing the sample and the reagent can be, for example, a super serpentine reactor, available from Global FIA, Inc Fox Island, Wash.

The means 1504 for transporting the sample and the reagent to a PCR reactor is operatively connected to the means 1503 for mixing the sample and the reagent. The means 1504 for transporting the sample and the reagent to a PCR reactor consists of a fluidics system. The means 1504 for transporting the sample and the reagent to a PCR reactor can be, for example, FEP tubing available from Cole-Parmer, Vernon Hills, Ill.

The means 1505 for performing PCR amplification is operatively connected to the means 1504 for transporting the sample and the reagent to a PCR reactor. This results in an amplified sample. In one embodiment the PCR amplification means 1505 includes an embedded thermocouple calibration conduit. PCR amplification devices are described in publications such as U.S. Pat. No. 5,589,136 for silicon-based sleeve devices for chemical reactions, assigned to the Regents of the University of California, inventors: M. Allen Northrup, Raymond P. Mariella, Jr., Anthony V. Carrano, and Joseph W. Balch, patented Dec. 31, 1996 and many are commercially available such as ABI PRISM® 7700 Sequence Detection System by Applied Biosystems; iCycler iQ Real-Time PCR Detection System by Bio-Rad; and Smart Cycler® System by Cepheid.

The means 1506 for transporting the amplified sample from the PCR reactor is operatively connected to the means 1205 for performing PCR amplification. The means 1506 for transporting the amplified sample from the PCR reactor can be, for example, FEP tubing available from Cole-Parmer, Vernon Hills, Ill.

The means 1507 for detection of PCR amplicon is operatively connected to the means 1506 for transporting the amplified sample from the PCR reactor. The means 1507 for detection of PCR amplicon can be, for example, a detection system described in publications and products produced by Cepheid and Baltimore-based Environmental Technologies Group, Inc. (ETG), a part of London-based Smiths Aerospace.

Conduits are included within the means 1501 for injecting and or aspirating a sample, means 1502 for adding PCR reagent to the sample, means 1503 for mixing the sample and the reagent, means 1504 for transporting the sample and the reagent to a PCR reactor, means 1505 for performing PCR amplification, means 1506 for transporting the amplified sample from the PCR reactor, and means 1507 for detection of PCR amplicon. A means 1508 for decontamination and conditioning the conduits is directly connected to the means 1507 for detection of PCR amplicon. The means 1508 for decontamination and conditioning the conduits is operatively connected to the means 1501 for injecting and or aspirating a sample, means 1502 for adding PCR reagent to the sample, means 1503 for mixing the sample and the reagent, means 1504 for transporting the sample and the reagent to a PCR reactor, means 1505 for performing PCR amplification, means 1506 for transporting the amplified sample from the PCR reactor, and means 1507 for detection of PCR amplicon. The decontamination and conditioning of all exposed conduits can be, for example, be performed by using a decontaminant, such as bleach, which is pumped through the exposed conduits and then washed from the system with a suitable wash solution.

Referring now to FIG. 16, a block diagram illustrates another embodiment of an autonomous pathogen detection system constructed in accordance with the present invention. This embodiment of an autonomous pathogen detection system is designated generally by the reference numeral 1600. The autonomous pathogen detection system 1600 provides water sample collection 1601, sample preparation 1602, and detection 1603 and 1604.

In operation, a water sample collection unit 1601 continuously samples a water source. Water sampling systems are known in the art. For example, a water sampling system is shown in U.S. Pat. No. 6,306,350 issued Oct. 23, 2001 titled water sampling method and apparatus with analyte integration. The disclosure of U.S. Pat. No. 6,306,350 is incorporated herein by reference.

The in-line sample preparation unit 1602 concentrates the sample in a swirling buffer solution. Particles of a given size distribution are selected by varying the flow rate across a separator unit. The in-line sample preparation system 1602 provides all sample preparation steps (i.e., mix, wash, incubation, etc.), and performing multiplex detection using a Luminex flow cytometer.

In the "detection" sub-system 1603, a collected sample is mixed with optically encoded microbeads. Each color of microbead contains a capture assay that is specific for a given bioagent. Fluorescent labels are added to identify the presence of each agent on the bound bead. Each optically encoded and fluorescently labeled microbead is individually read in a flow cytometer, and fluorescent intensities are then correlated with bioagent concentrations.

In the "confirmation" sub-system 1604, PCR (nucleic acid) amplification and detection confirms the presence of the bioagent. An archived sample is mixed with the Taqman reagent, and then introduced by a SIA system into a flow through polymerase chain reaction (PCR) system. Specific nucleic acid signatures associated with the targeted bioagent are amplified and detected using fluorescence generated from nucleic acid replication from the Taqman probes. In the "Integrated Remote Control and Feedback" sub-system 1605, a central computer uses a simple serial based Labview control system to control all instrument functions. A software system provides data acquisition, real time data analysis, and result reporting via a graphical user interface.

The first stage of the system 1600 is "water sample collection 1601" that provides collection of particles from a source of water that could contain bioagents. The water sample collection system 1601 and in-line sample preparation 1602 provide preconcentration and delivery of the particles of interest to a wetted wall cyclone collector. The separator system captures particles of interest.

In the wetted wall cyclone collector, the particles are collected in a fluid, making downstream processing much easier. An on board computer controls water flow rates and the size range of particles collected. A particle counter provides reap-time feedback on the size and quantity of particles collected.

Particles are drawn into the system that is designed to only allow the collection of particles of a pre-set size. The pre-set size can be selected as desired. The system is designed to only collect particles that are desired. The accepted particles continue on into a separator section that returns all the particles that are not of the desired size back into the environment. The remaining particles, are known as the product, flow. The product flow continues into the detection sections.

The system 1600 has the capability to measure particle sizes in the sampling environment via a built in particle counter with four size ranges, and can store and display the results in real-time. The system is entirely self-contained requiring only a power connection. The on-board computer has high-speed communications capability allowing networks of these sampling systems to be remotely operated.

The 1600 is useful for many application of water sampling. The system 1600 can be used to sample water quality in public buildings, for sampling in food processing facilities, for use in monitoring agricultural areas for the presence of pollens or pesticides and other water sampling uses.

Referring now to FIG. 17, a block diagram illustrates another embodiment of an autonomous pathogen detection system constructed in accordance with the present invention. This embodiment of an autonomous pathogen detection system is designated generally by the reference numeral 1700. The autonomous pathogen detection system 1700 provides soil sample collection 1701, sample preparation 1702, and detection 1703 and 1704.

In operation, a soil sample collection unit 1701 continuously samples a soil source. Soil sampling systems are known in the art. For example, a soil sampling system is shown in U.S. Pat. No. 6,363,803 titled, vehicle mounted soil sampler invented by Elmer Hubers, patented Apr. 2, 2002. The disclosure of U.S. Pat. No. 6,363,803 is incorporated herein by reference.

The in-line sample preparation unit 1702 concentrates the sample in a swirling buffer solution. Particles of a given size distribution are selected by varying the flow rate across a separator unit. The in-line sample preparation system 1702 provides all sample preparation steps (i.e., mix, wash, incubation, etc.), and performing multiplex detection using a Luminex flow cytometer.

In the "detection" sub-system 1703, a collected sample is mixed with optically encoded microbeads. Each color of microbead contains a capture assay that is specific for a given bioagent. Fluorescent labels are added to identify the presence of each agent on the bound bead. Each optically encoded and fluorescently labeled microbead is individually read in a flow cytometer, and fluorescent intensities are then correlated with bioagent concentrations.

In the "confirmation" sub-system 1704, PCR (nucleic acid) amplification and detection confirms the presence of the bioagent. An archived sample is mixed with the Taqman reagent, and then introduced by a SIA system into a flow through polymerase chain reaction (PCR) system. Specific nucleic acid signatures associated with the targeted bioagent are amplified and detected using fluorescence generated from nucleic acid replication from the Taqman probes. In the "Integrated Remote Control and Feedback" sub-system 1705, a central computer uses a simple serial based Labview control system to control all instrument functions. A software system provides data acquisition, real time data analysis, and result reporting via a graphical user interface.

The first stage of the system 1700 is "soil sample collection 1701" that provides collection of particles from a source of soil that could contain bioagents. The soil sample collection system 1701 and in-line sample preparation 1702 provide preconcentration and delivery of the particles of interest to a wetted wall cyclone collector. The separator system captures particles of interest.

In the wetted wall cyclone collector, the particles are collected in a fluid, making downstream processing much easier. An on board computer controls soil flow rates and the size range of particles collected. A particle counter provides reap-time feedback on the size and quantity of particles collected.

Particles are drawn into the system that is designed to only allow the collection of particles of a pre-set size. The pre-set size can be selected as desired. The system is designed to only collect particles that are desired. The accepted particles continue on into a separator section that returns all the particles that are not of the desired size back into the environment. The remaining particles, are known as the product, flow. The product flow continues into the detection sections.

The system 1700 has the capability to measure particle sizes in the sampling environment via a built in particle counter with four size ranges, and can store and display the results in real-time. The system is entirely self-contained requiring only a power connection. The on-board computer has high-speed communications capability allowing networks of these sampling systems to be remotely operated. The 1700 is useful for many application of soil sampling. The system 1700 can be used to sample soil quality in monitoring agricultural areas for the presence of pollens or pesticides and other soil sampling uses.

In operation of the pathogen detection system, the in-line nucleic acid amplification and detection system provides nucleic acid assay methods. The methods include a number of steps. One step consists of automatically injecting and or aspirating a sample. Another step consists of automatically adding PCR reagent to the sample. Another step consists of automatically mixing the sample and the reagent. Another step consists of automatically transporting the sample and the reagent to a PCR reactor. The PCR reactor consists of a fluidics system. Another step consists of automatically performing PCR amplification resulting in an amplified sample. Another step consists of automatically transporting the amplified sample from the PCR reactor. Another step consists of automatically detecting PCR amplicon. The method is performed in a nucleic acid assay system and the nucleic acid assay system is decontaminated and conditioned before a new sample is analyzed.

The system includes both real time and post-PCR detection. The system is ideal for monitoring type systems, such as those currently being developed to detect terrorist releases of aerosolized bioagents. On-site detection systems for infectious diseases under development will need to incorporate sample preparation and analysis functions. The system allows relatively unskilled personnel, such as early responders, to perform real-time field or point-of-care nucleic acid assays. In various other embodiments of the autonomous pathogen detection system, the confirmation of bioagent(s) in the sample is provided by a multiplex immunoassay detector, a multiplex PCR detector, and a real time PCR detector.

The present invention provides an Autonomous Pathogen Detection System (APDS) for monitoring the environment to protect the public from the release of hazardous biological agents. The Autonomous Pathogen Detection System is a countermeasure to bioterrorism, one of the most serious threats to the safety of United States citizens, citizens of other countries, and the military.

The APDS program was initiated to fill the requirement of a distributed environmental monitoring system for civilian applications. Multiplexed assays are used to reduce reagent costs, making long term monitoring operations possible (e.g., U.S. Postal Service mail screening). A unique, orthogonal detection approach that combines antibody-based and nucleic acid-based assays reduces false positives to a very low level. Antibody assays allow the detector to respond to all types of bioagents, including those without nucleic acids such as protein toxins. Nucleic acid assays allow much more sensitive detection, reducing the number of sensors needed to protect a given area. The fully autonomous aerosol collection and sample preparation capabilities limit maintenance requirements and makes integration into a central security or monitoring network possible.

The Department of Transportation is actively seeking space, providing monitoring biomonitoring systems for protection of capabilities for Special Events, transportation hubs, with airports residing at the facilities, transportation centers, top of this list. The system is capable of meeting these needs.

There are other environmental or clinical pathogen detection system needs. Mobile units could be transported to suspected "sick buildings" to test for mold or fungal spores that might be causing tenant illnesses. Units with reagents for animal diseases could be placed in livestock transport centers or feedlots to rapidly detect airborne pathogens and protect against disease outbreaks. Monitors in hospitals could be used to test for airborne spread of contagious materials among patients. The system could be used at high profile events such as the Olympics for short-term, intensive monitoring or more permanent installation in major public buildings or transportation nodes. All of the individual units can be networked to a single command center so that a small group of technical experts can maintain and respond to alarms at any of the units. The system is capable of meeting all of these needs.

The primary needs describe above are directed to protection of civilians from terrorist attacks. The system also has uses in protecting military personnel from biological warfare attacks. The military continues to evaluate options to their current biowarfare detection systems and the system meets many of the needs of the military.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of monitoring air for bioagents, the air containing potential bioagent particles of various sizes, consisting the steps of:

gathering said air containing potential bioagent particles of various sizes by forming a flow stream of the air containing potential bioagent particles of various sizes;

directing said flow stream of the air through a slot that only admits the potential bioagent particles of various sizes that are smaller than a predetermined size;

using a virtual impactor for separating said potential bioagent particles of various sizes that are smaller than said predetermined size into a further separation by size range that are likely to contain said bioagents and collecting said potential bioagent particles of a size range that are likely to contain said bioagents by causing said flow stream to change directions in said virtual impactor wherein some of the potential bioagent particles of various sizes do not change directions leaving only potential bioagent particles of a size range that are likely to contain said bioagents;

collecting said bioagents in said potential bioagent particles of a size range that are likely to contain said bioagents by directing said potential bioagent particles of a size range that are likely to contain said bioagents from said virtual impactor to a fluid wetted-wall cyclone collector wherein said potential bioagent particles of a size range that are likely to contain said bioagents are concentrated in a volume of said fluid between two cubic centimeters and seven cubic centimeters and, detecting said bioagents in said potential bioagent particles of a size range that are likely to contain said bioagents in said volume of fluid between two cubic centimeters and seven cubic centimeters in said wetted-wall cyclone collector by mixing optically encoded microbeads coded with fluorescently labeled antibodies with said potential bioagent particles of a size range that are likely to contain said bioagents and detecting said bioagents with said optically encoded microbeads coded with fluorescently labeled antibodies with a laser.

2. A method of monitoring air for bioagents, the air containing potential bioagent particles of various sizes, consisting of the steps of:

gathering said air containing potential bioagent particles of various sizes by forming a flow stream of the air containing potential bioagent particles of various sizes;

directing said flow stream of the air through a slot that only admits the potential bioagent particles of various sizes that are smaller than a predetermined size;

using a virtual impactor for separating said potential bioagent particles of various sizes that are smaller than said predetermined size into a further separation by size range that are likely to contain said bioagents and collecting said potential bioagent particles of a size range that are likely to contain said bioagents by causing said flow stream to change directions in said virtual impactor wherein some of the potential bioagent particles of various sizes do not change directions leaving only potential bioagent particles of a size range that are likely to contain said bioagents;

collecting said bioagents in said potential bioagent particles of a size range that are likely to contain said bioagents by directing said potential bioagent particles of a size range that are likely to contain said bioagents from said virtual impactor to a water wetted-wall cyclone collector wherein said potential bioagent particles of a size range that are likely to contain said bioagents are concentrated in a volume of said water between two cubic centimeters and seven cubic centimeters;

detecting said bioagents in said potential bioagent particles of a size range that are likely to contain said bioagents in said volume of water between two cubic centimeters and seven cubic centimeters in said wetted-wall cyclone collector by mixing optically encoded microbeads coded with fluorescently labeled antibodies with said potential bioagent particles of a size range that are likely to contain said bioagents and detecting said bioagents with said optically encoded microbeads coded with fluorescently labeled antibodies with a laser, and confirming said bioagents of a size range that are likely to contain said bioagents by adding PCR reagent to said potential bioagent particles of a size range that are likely to contain said bioagents, performing PCR amplification on said potential bioagent particles of a size range that are likely to contain said bioagents, and detecting PCR amplicon in said potential bioagent particles of a size range that are likely to contain said bioagents.

\* \* \* \* \*